(12) United States Patent
Banchereau et al.

(10) Patent No.: US 7,988,963 B1
(45) Date of Patent: Aug. 2, 2011

(54) USE OF ALLOGENEIC CELL LINES TO LOAD ANTIGEN PRESENTING CELLS TO ELICIT OR ELIMINATE IMMUNE RESPONSES

(75) Inventors: Jacques F. Banchereau, Dallas, TX (US); Frederic Berard, Saint Genis Laval (FR); Patrick Blanco, Talence (FR); Eve-Marie Neidhart-Berard, Saint Genis Laval (FR); Mahyar Nouri-Shirazi, Dallas, TX (US); Anna Karolina Palucka, Dallas, TX (US)

(73) Assignee: Baylor Research Institute, Dallas, TX (US)

( * ) Notice: Subject to any disclaimer, the term of this patent is extended or adjusted under 35 U.S.C. 154(b) by 432 days.

(21) Appl. No.: 10/110,553

(22) PCT Filed: Oct. 16, 2000

(86) PCT No.: PCT/US00/28670
§ 371 (c)(1),
(2), (4) Date: Aug. 30, 2002

(87) PCT Pub. No.: WO01/29192
PCT Pub. Date: Apr. 26, 2001

(51) Int. Cl.
*A61K 35/14* (2006.01)
*C12N 5/078* (2010.01)
*C12N 5/0784* (2010.01)
*C12N 5/0786* (2010.01)
*C12N 5/0783* (2010.01)

(52) U.S. Cl. ............. 424/93.71; 435/373; 435/377

(58) Field of Classification Search ............ None
See application file for complete search history.

(56) References Cited

U.S. PATENT DOCUMENTS

| | | | |
|---|---|---|---|
| 5,637,483 A | 6/1997 | Dranoff et al. | |
| 5,851,756 A | 12/1998 | Steinman et al. | |
| 6,077,519 A * | 6/2000 | Storkus et al. | 424/277.1 |
| 6,602,709 B1 * | 8/2003 | Albert et al. | 435/372 |

FOREIGN PATENT DOCUMENTS

| | | |
|---|---|---|
| WO | WO 9532734 | 12/1995 |
| WO | WO 9852582 | 11/1998 |
| WO | WO 9942564 | 8/1999 |
| WO | WO2004/015056 | * 2/2004 |

OTHER PUBLICATIONS

Van Gool et al (Journal of Experimental Medicine, 1994, vol. 179, pp. 715-720).*
Zakeri et al, Cell Death and Differentiation, 2000, vol. 7, pp. 1276-1277.*
Diaz et al, Cell Death and Differentiation, 2005, vol. 12, pp. 1449-1456.*
Papucci et al, Vol. Cell and Tissue Research, 2004, vol. 316, pp. 197-209.*
Fulda et al, Journal of Biological Chemistry, 1998, vol. 273, pp. 33942-33948.*
Gjertsen et al (International Journal of Cancer, 1997, vol. 72, pp. 784-790).*
Frey (Journal of Immunology, 1995, vol. 154, pp. 4613-4622).*
Fields et al (PNAS, 1998, vol. 95, pp. 9482-9487).*
Borkowski et al (European Journal of Immunology, 196, vol. 26, pp. 110-114).*
Albert et al. 1998. "Dendritic cells acquire antigen from apoptotic cells and induce class I-restricted CTLs," *Nature* 392 86.
Albert et al 1998. "Tumor-specific killer cells in paraneoplastic cerebellar degeneration," *Nat Med* 4 1321.
Banchereau J and Steinman R M 1998 "Dendritic cells and the control of immunity," *Nature* 392 245.
Bell et al, 1999 "Dendritic cells," *Adv Immunol* 72 255.
Boczkowsi et al 1996 "Dendritic cells pulsed with RNA are potent antigen-presenting cells in vitro and in vivo," *J Exp Med* 184 465.
Cella. el al. 1997 "Origin, maturation and antigen presenting function of dendritic cells," *Curr Opin Immunol* 9 10.
Celluzza et al. 1996 "Peptide-pulsed dendritic cells induce antigen-specific, CTL-mediated protective tumor immunity," *J Exp Med* 183-283.
Chang J.W.C. et al 1999 "Induction of Th1 response by dendritic cells pulsed by autologous melanoma apoptotic bodies," *Proceeding of the American Association for Cancer Research*, vol. 40, Mar. 1999, p. 86.
Fields et al 1998 "Murine dendritic cells pulsed with whole tumor lysales mediate potent immune responses in vitro and in vivo," *Proc. Natl Acad Sci USA* 95 9482.
Gilboa, E et al 1998 "Immunology of cancer with dendritic cell-based vaccines," *Cancer Immunol Immunother* 46.82.
Gong et al. 1998, "Reversal of tolerance to human MUCI antigen in MUCI transgenic mice immunized with fusions of dendritic and carcinoma cells," *Proc Natl Acad Sci USA* 95.6279.
Henry, F et al 1999 "Antigen-presenting cells that phagocytose apoptotic tumor-derived cells are potent tumor vaccines," *Cancer Research* 59 3329-32.
Hsu, et al. 1996, "Vaccination of patients with B-cell lymphoma using autologous antigen-pulsed dendritic cells," *Nat. Med* 2 52.
Mayordomo, et al. 1995 "Bone marrow-derived dendritic cells pulsed with synthetic tumor peptides elicit protective and therapeutic antitumor immunity," *Nat Med* 1 1297.
Mukherji, et al 1995 "Induction of antigen-specific cytolytic T cells in situ in human melanoma by immunization with synthetic peptide-pulsed autologous antigen presenting cells," *Proc Natl Acad Sci USA* 92.8078.

(Continued)

*Primary Examiner* — Karen Canella
(74) *Attorney, Agent, or Firm* — Chalker Flores, LLP; Edwin S. Flores; Chainey P. Singleton

(57) ABSTRACT

Novel antigen-presenting cells, including but not limited to dendritic cells, that are loaded with antigens from dead or dying cells including allogenic cell lines, and the methods for making such antigen-presenting cells are described. These loaded antigen-presenting cells induce therapeutic immune responses in humans. Such loaded antigen-presenting cells are useful in the management of cancer. Antigen-loaded dendritic cells prepared as described here can prime naïve T cells to differentiate into effector cells able to recognize multiple and/or shared tumor antigens that are expressed either on the tumor cells that are used to load the dendritic cells and/or on other tumor cells. The cytotoxic T cells generated by exposure to antigen-loaded dendritic cells prepared as described here can be used in adoptive therapy. This induction of responses against multiple antigens shared between different cells, for instance tumor cells, as described here is important as it leads to broad immune responses.

15 Claims, 29 Drawing Sheets

OTHER PUBLICATIONS

Nestle, et al. 1998 "Vaccination of melanoma patients with peptide—or tumor Iysate-pulsed dendritic cells," *Nat Med* 4 328.

Sogn, JA. 1998 "Tumor immunology, the glass is half full," *Immunity* 9 757.

Song et al 1997 "Dendritic cells genetically modified with an adenovirus vector encoding the cDNA for a model antigen induce protective and therapeutic antitumor immunity," *J Exp Med* 186 1247.

Specht et al 1997 "Dendritic cells retrovirally transduced with a model antigen gene are therapeutically effective against established pulmonary metastases," *J Exp Med* 186 1213.

Toja, et al 1998 "Evaluation of phase I/II clinical trials in prostate cancer with dendritic cells PSMA peptides," *Prostate* 36:39.

Zitvogel, et al 1996 "Therapy of murine tumors with peptide-pulsed dendritic cells dependence on T cells, B7 constitnulation and T helper cell t-associated cytokines," *J Exp Med* 183 87.

Extended European Search Report for EP 09014698.6 dated Dec. 29, 2009.

Hackstein, H., et al., "Designer dendritic cells for tolerance induction: guided not misguided missles," Trends in Immunology (2001), 22:437-442.

Verhasselt, V., et al., "N-Acetyl-L-Cysteine Inhibits Primary Human T Cell Responses at the Dendritic Cell Level: Association with NF-kB Inhibition," Journal of Immunology (1999), 162:2569-2574.

\* cited by examiner

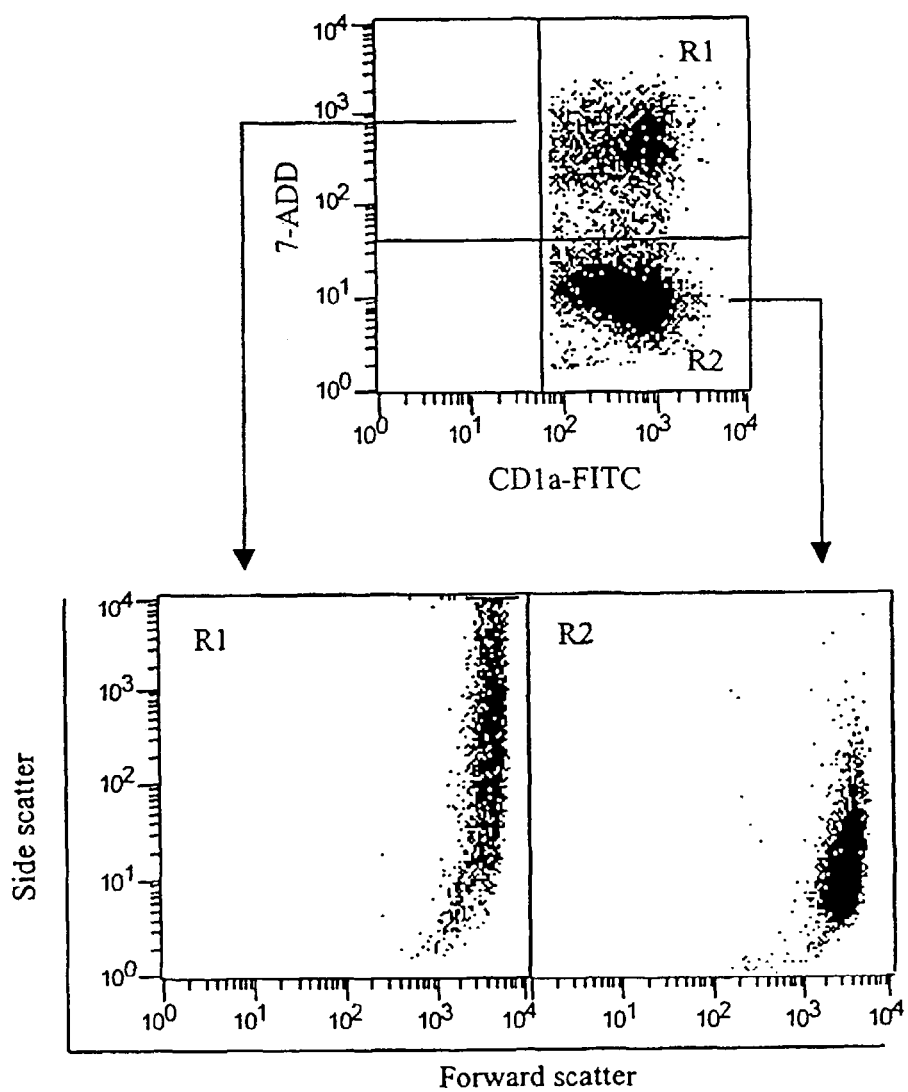

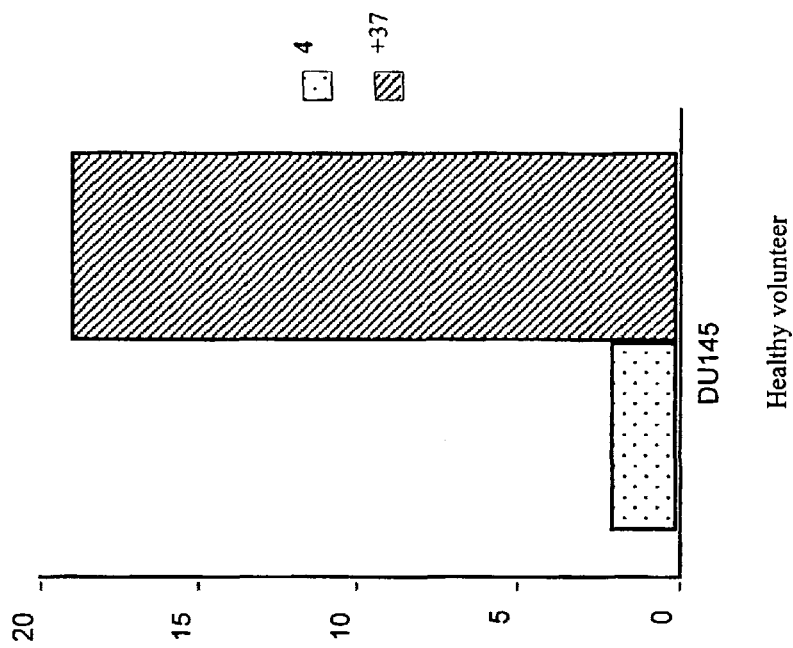
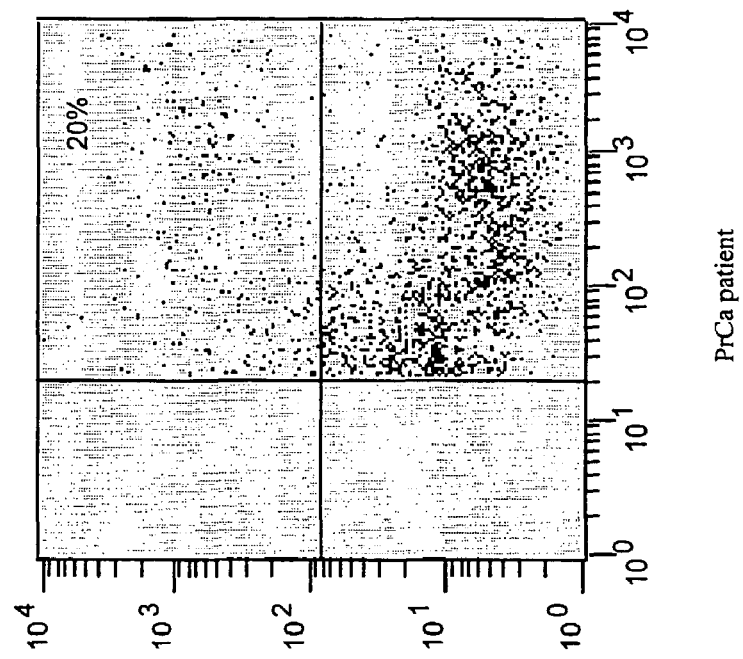

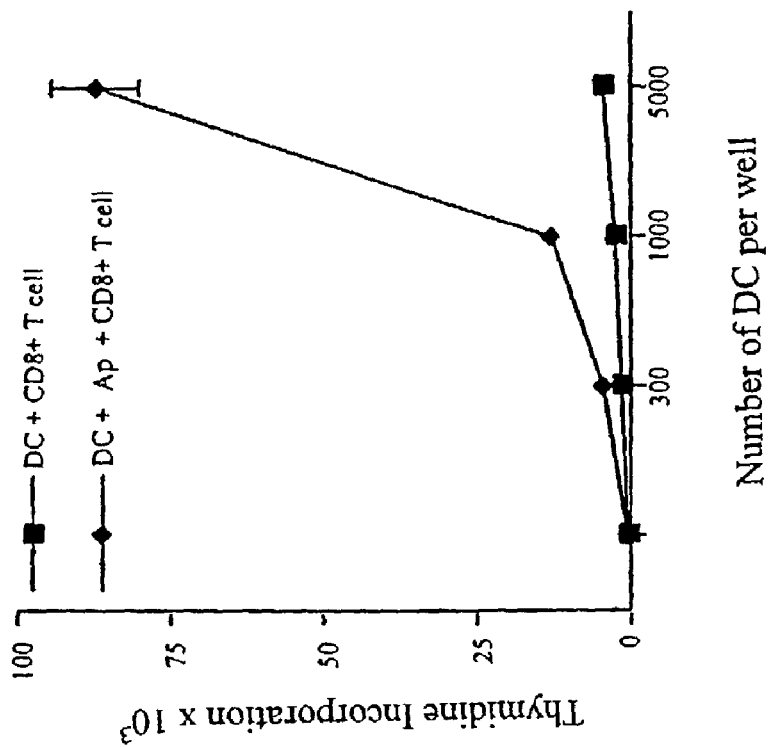
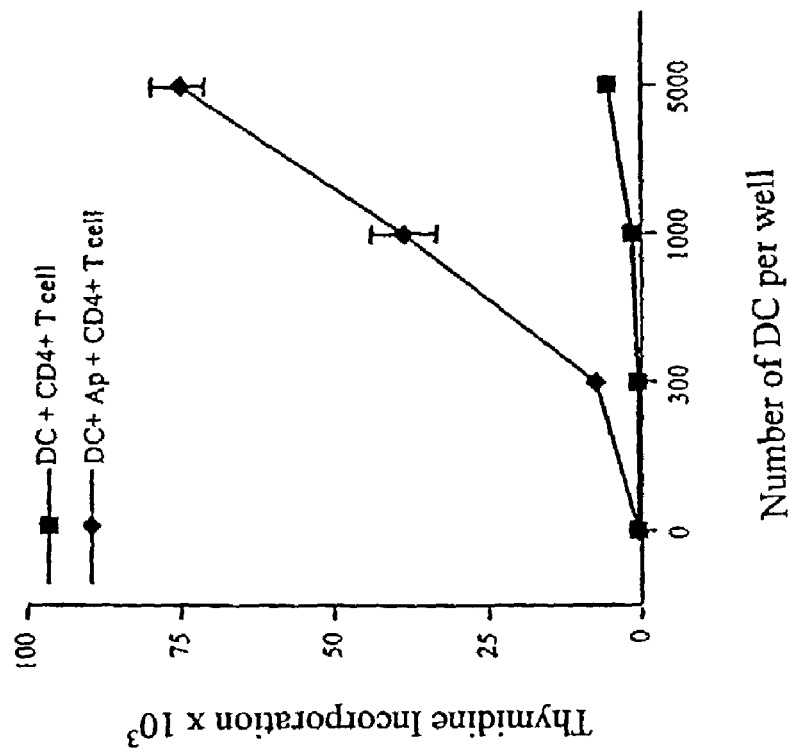

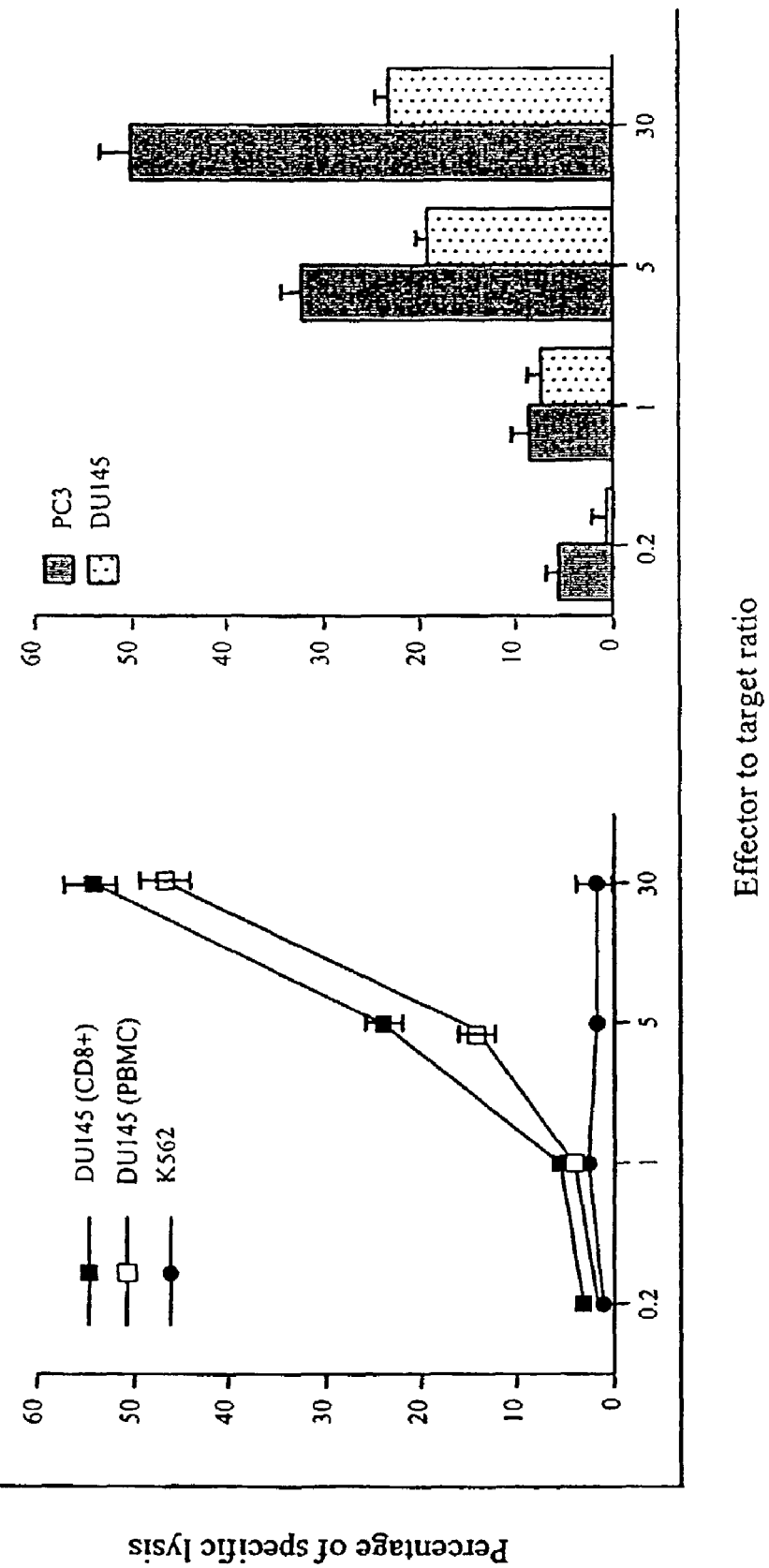

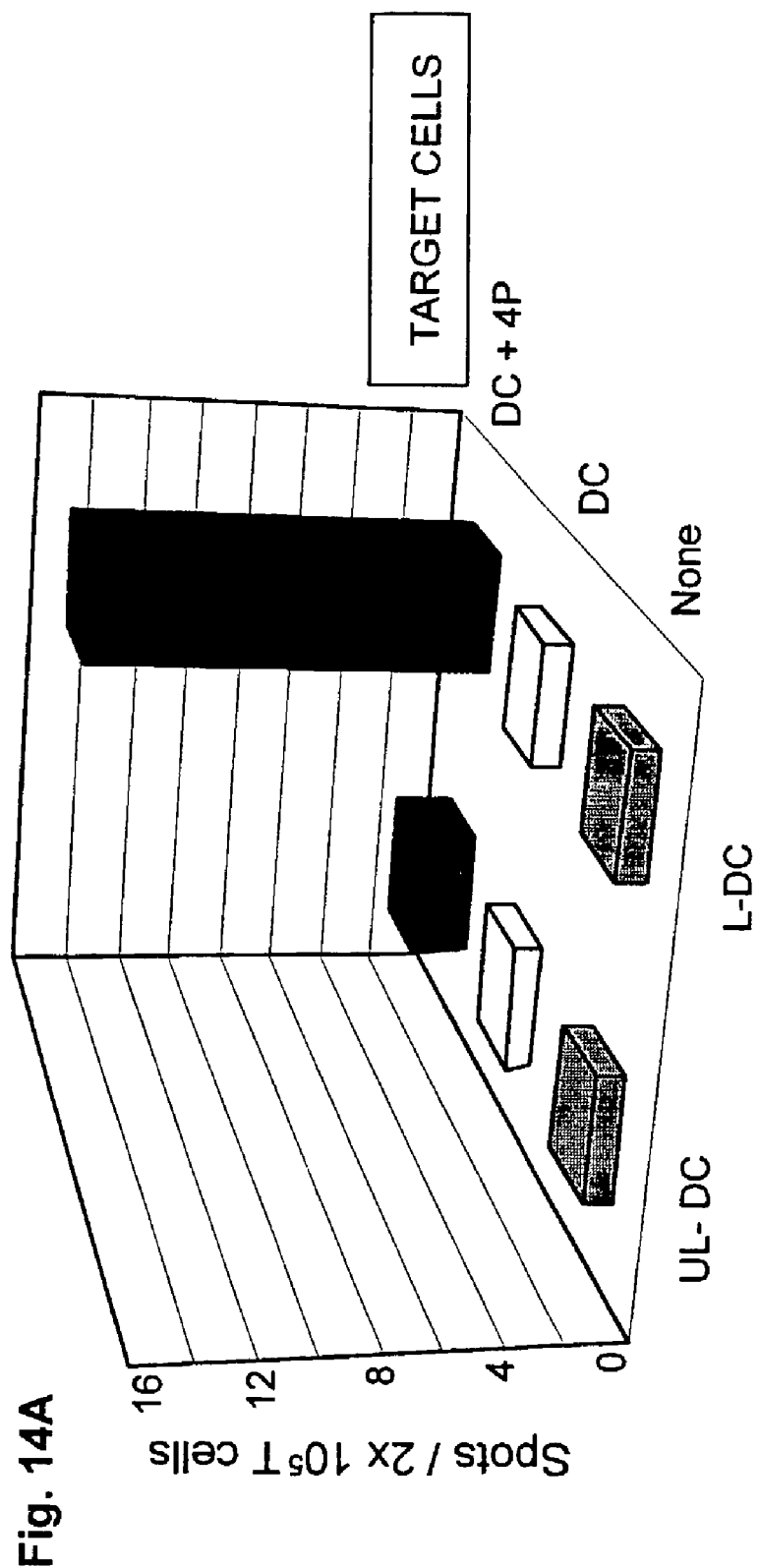

USE OF ALLOGENEIC CELL LINES TO LOAD ANTIGEN PRESENTING CELLS TO ELICIT OR ELIMINATE IMMUNE RESPONSES

STATEMENT OF FEDERALLY FUNDED RESEARCH

This invention was made with U.S. Government support under Contract No. RO1 CA78846A awarded by the NIH. The government has certain rights in this invention.

TECHNICAL FIELD OF INVENTION

This invention relates to engineering immunogenic cells.

BACKGROUND

Dendritic cells (hereinafter referred to as "DC") are the only antigen-presenting cells, or APC, able to induce primary immune responses (Cella, et al. 1997. "Origin, maturation and antigen presenting function of dendritic cells," *Curr Opin Immunol* 9:10; Banchereau, J., and R. M. Steinman. 1998. "Dendritic cells and the control of immunity," *Nature* 392: 245). Circulating DC precursors circulate to tissues where they reside as immature, antigen-capturing cells with high endocytic and phagocytic activity. Following antigen uptake, DC migrate to the secondary lymphoid organs where they mature and become antigen-presenting cells able to select and activate naïve antigen-specific CD4+ T cells. This permits diversification of the response and activation of antigen-specific effectors such as antigen-specific cytotoxic T lymphocytes (hereinafter referred to as "CTL") and B cells as well as non-specific effectors such as NK cells, macrophages and eosinophils (Sogn, J. A. 1998. "Tumor immunology: the glass is half full," *Immunity* 9:757).

DC have been used to elicit an immune response against tumors. The induction of tumor immunity can be viewed as a three-step process that includes: 1) presentation of tumor associated antigens; 2) selection and activation of tumor associated antigens—specific T cells as well as non-specific effectors; 3) localizing tumor associated antigens—specific T cells to the tumor site; and 4) recognition of restriction elements leading to the elimination of tumor cells. U.S. Pat. No. 5,637,483 issued to Dranoff et al. discloses a method by which modified tumor cells expressing cytokines such as GM-CSF and IL-2 are irradiated or rendered proliferation incompetent and then administered to a patient to act as a stimulator or suppressor of a patient's systemic immune system. Experiments in mice have demonstrated the development of both protective and therapeutic anti-tumor responses induced by DC loaded with tumor associated antigens (Bell, et al. 1999. "Dendritic cells," *Adv Immunol* 72:255). Furthermore, pilot clinical trials in humans show the feasibility of DC administration and the ability of peptide-loaded DC to induce peptide-specific T cell responses in patients with lymphoma, malignant melanoma and prostate carcinoma (Mukherji, et al. 1995. "Induction of antigen-specific cytolytic T cells in situ in human melanoma by immunization with synthetic peptide-pulsed autologous antigen presenting cells," *Proc Natl Acad Sci USA* 92:8078; Hsu, et al. 1996. "Vaccination of patients with B-cell lymphoma using autologous antigen-pulsed dendritic cells," *Nat Med* 2:52; Gilboa, E., et al. 1998. "Immunotherapy of cancer with dendritic-cell-based vaccines," *Cancer Immunol Immunother* 46:82; Nestle, et al. 1998. "Vaccination of melanoma patients with peptide- or tumor lysate-pulsed dendritic cells," *Nat Med* 4:328; Tjoa, et al. 1998. "Evaluation of phase I/II clinical trials in prostate cancer with dendritic cells and PSMA peptides," *Prostate* 36:39).

In order for DC to affect the immune system, the cells must possess processed peptide fragments to interact with T-cells, or be "loaded." One of the critical challenges for the use of DC as immunotherapy vectors is the identification of an efficient antigen loading strategy. Several systems have been employed to deliver tumor associated antigens to DC including: 1) defined peptides of known sequences (Mayordomo, et al. 1995. "Bone marrow-derived dendritic cells pulsed with synthetic tumor peptides elicit protective and therapeutic antitumor immunity," *Nat Med* 1:1297; Celluzzi, et al. 1996. "Peptide-pulsed dendritic cells induce antigen-specific CTL-mediated protective tumor immunity," *J Exp Med* 183:283); 2) undefined acid-eluted peptides from autologous tumor (Zitvogel, et al. 1996. "Therapy of murine tumors with tumor peptide-pulsed dendritic cells: dependence on T cells, B7 costimulation, and T helper cell 1-associated cytokines," *J Exp Med* 183:87); 3) whole tumor lysates (Fields, et al. 1998. "Murine dendritic cells pulsed with whole tumor lysates mediate potent antitumor immune responses in vitro and in vivo," *Proc Natl Acad Sci USA* 95:9482); 4) retroviral and adenoviral vectors (Song, et al. 1997. "Dendritic cells genetically modified with an adenovirus vector encoding the cDNA for a model antigen induce protective and therapeutic antitumor immunity," *J Exp Med* 186:1247; Specht, et al. 1997. "Dendritic cells retrovirally transduced with a model antigen gene are therapeutically effective against established pulmonary metastases," *J Exp Med* 186:1213); 5) tumor cell derived RNA (Boczkowski, et al. 1996. "Dendritic cells pulsed with RNA are potent antigen-presenting cells in vitro and in vivo," *J Exp Med* 184:465); and 6) fusion of DC with tumor cells (Gong, et al. 1998. "Reversal of tolerance to human MUCI antigen in MUCI transgenic mice immunized with fusions of dendritic and carcinoma cells, *Proc Natl Acad Sci USA* 95:6279).

Although all methods for delivering tumor associated antigens described above induce T cell responses and cause considerable anti-tumor effects, each has potential drawbacks (Sogn, J. A. 1998. "Tumor immunology: the glass is half full," *Immunity* 9:757). Foremost, peptide-based strategies are limited by 1) the knowledge of the MHC haplotype of each patient; 2) the knowledge of the corresponding MHC class I binding motifs of the tumor associated antigens; 3) the variability of the MHC class I binding affinity of the synthetic peptides; and 4) the knowledge of whether or which various defined peptides represent tumor associated antigens in vivo.

Unlike a peptide-based approach which requires information about MHC haplotype and peptide sequence, unfractionated tumor tissue can provide both MHC class I and MHC class II epitopes without identifying tumor associated antigens. Recent studies demonstrated the ability of DC to capture dead or dying cells and elicit MHC class I-restricted secondary CTL responses (Albert, et al. 1998. "Dendritic cells acquire antigen from apoptotic cells and induce class I-restricted CTLs," *Nature* 392:86; Albert, et al. 1998. "Tumor-specific killer cells in paraneoplastic cerebellar degeneration," *Nat Med* 4:1321). These studies indicated that 1) DC loaded with dead or dying influenza virus-infected cells can activate lymphocytes to mount virus-specific CTL responses; and 2) DC that capture dead or dying tumor cells can present antigen to tumor associated antigens peptide-specific T cells that were derived from patients with the paraneoplastic cerebellar degeneration. Because of the potential of engineered DC to contribute positively in the treatment of human disease, a simple method is desired for their production.

U.S. Pat. No. 5,851,756 issued to Steinman et al. discloses methods by which proliferating cultures of DC precursors and mature DC can be produced in vitro. Steinman et al. disclose the production of T cell dependent antigens using mature DC cultures, wherein the antigens are comprised of DC modified antigens or antigen-activated DC. Steinman et al. further disclose that the DC modified antigens or antigen-activated DC can be used as immunogens for vaccines or treatment of infectious diseases.

Major problems in tumor immunotherapy as experienced in the methods presented above are the limited number of well-defined tumor associated antigens and the lack of evidence that the known tumor associated antigens actually represent rejection antigens in vivo. Furthermore, the use of MHC class I binding peptides is associated with the HLA restriction and the limitation of induced immune responses to $CD8^+$ T cells. In this context, the use of unfractionated antigenic material, in the form of dead or dying allogeneic tumor cells, that provides both MHC class I and class II epitopes leading to a diversified immune response involving many clones of $CD4^+$ T cells and CTL represents an attractive alternative.

International Application No. WO 99/42564 of Albert et al. discloses methods directed toward developing therapies for increasing patient immunity to chronic infections and tumors by inducing tumor or infected cells to undergo apoptosis, having the apoptotic tumor or infected cells gain access to phagocytic, maturing dendritic cells, and exposing the apoptotic cell-primed dendritic cells expressing antigen of interest to T cells in vivo or in vitro for the induction of antigen-specific T cell responses.

We have now developed a method for engineering immunogenic DC. We have perfected a process using immature human antigen-presenting cells, including DC, derived from healthy volunteers and from patients that can capture dead or dying allogeneic cells, and subsequently present their antigens to autologous T cells, thus inducing proliferation of autologous $CD4^+$ T cells and $CD8^+$ t cells. Furthermore, by using the processes described herein, it has been found that DC loaded with allogeneic tumor cells can activate $CD8^+$ T cells, generate CTL specific for antigens expressed by the dead or dying cells, and also recognize antigens that are shared between different tumor cell lines. Yet another finding is that by using the process described herein, DC loaded with dead or dying allogeneic tumor cell lines can prime naïve T cells and induce their differentiation to antigen-specific CTL.

SUMMARY OF THE INVENTION

In one aspect, the invention is a method of inducing tumor specific immune response in a tumor-bearing patient comprising isolating antigen-presenting cells from the patient, coincubating the antigen-presenting cells with dead or dying cell portions possessing at least one tumor antigen to form loaded antigen-presenting cells, and administering the loaded antigen-presenting cells to the patient, wherein the patient's cells upon contact with the loaded antigen-presenting cells mature to form cytotoxic cells expressing cytotoxic activity against the tumor cells. The dead or dying cell portions can be obtained from allogeneic cell lines. The tumor specific immune response can be directed against the specific tumor antigen, multiple tumor antigens, or shared tumor antigens. The antigen-presenting cells can be at various stages of differentiation and/or maturation and are selected from the group consisting of dendritic cells, progenitors or precursors of dendritic cells from which dendritic cells are generated ex vivo, lymphoid dendritic cells, myeloid dendritic cells, interstitial dendritic cells, and Langerhans cells. The resulting cytotoxic cells can be either CD4 positive, CD8 positive or both.

In another aspect, the invention is a method of inducing tumor specific responses in a tumor-bearing patient comprising isolating antigen-presenting cells and cytotoxic cell precursors from the patient, coincubating antigen-presenting cells with dead or dying cell portions possessing at least one tumor antigen to form loaded-antigen-presenting cells, coculturing the loaded antigen-presenting cells with cytotoxic cell precursors isolated from the patient under conditions for their maturation to form cytotoxic cells, and administering the cytotoxic cells to the patient, wherein the cytotoxic cells express cytotoxic activity against the tumor cells. The dead or dying cell portions can be obtained from allogeneic cell lines. The tumor specific immune response can be directed against the specific tumor antigen, multiple tumor antigens, or shared tumor antigens. The antigen-presenting cells can be at various stages of differentiation and/or maturation and are selected from the group consisting of dendritic cells, progenitors or precursors of dendritic cells from which dendritic cells are generated ex vivo, lymphoid dendritic cells, myeloid dendritic cells, interstitial dendritic cells, and Langerhans cells. The resulting cytotoxic cells can be either CD4 positive, CD8 positive or both.

In another aspect, the invention is a method of inducing tumor specific responses in a tumor-bearing patient comprising coincubating antigen-presenting cells with dead or dying cell portions possessing at least one tumor antigen to form loaded antigen-presenting cells, coculturing the loaded antigen-presenting cells with naïve T cells under conditions for T cell maturation to form cytotoxic T cells, and administering the cytotoxic T cells to the patient, wherein the cytotoxic T cells express cytotoxic activity against the tumor cells. The dead or dying cell portions can be obtained from allogeneic cell lines. The tumor specific immune response can be directed against the specific tumor antigen, multiple tumor antigens, or shared tumor antigens. The antigen-presenting cells can be at various stages of differentiation and/or maturation and are selected from the group consisting of dendritic cells, progenitors or precursors of dendritic cells from which dendritic cells are generated ex vivo, lymphoid dendritic cells, myeloid dendritic cells, interstitial dendritic cells, and Langerhans cells. The resulting cytotoxic cells can be either CD4 T cells, CD8 T cells or both.

In another aspect, the invention is a method for mounting an immune response mediated by cytotoxic T cells comprising coincubating antigen-presenting cells with dead or dying cell portions possessing at least one antigen to which the immune response is desired to form loaded antigen-presenting cells, coculturing the loaded antigen-presenting cells with naïve T cells under conditions for T cell maturation to form cytotoxic T cells, and contacting the cytotoxic T cells with target cells possessing the antigen, wherein the cytotoxic T cells express cytotoxic activity against the target cells possessing the antigen. The target cells can be contacted in vitro. The method is useful wherein novel tumor rejection antigens can be identified. The antigen-presenting cells can be at various stages of differentiation and/or maturation and are selected from the group consisting of dendritic cells, progenitors or precursors of dendritic cells from which dendritic cells are generated ex vivo, lymphoid dendritic cells, myeloid dendritic cells, interstitial dendritic cells, and Langerhans cells.

In another aspect, the invention is a method of administering loaded antigen-presenting cells to a patient comprising isolating antigen-presenting cells from the patient, coincubating the antigen-presenting cells with dead or dying cell portions possessing at least one tumor antigen to form loaded antigen-presenting cells, administering the loaded antigen-presenting cells to the patient.

In another aspect, the invention is a method of administering tumor specific cytotoxic cells to a patient comprising isolating antigen-presenting cells and cytotoxic cell precursors from the patient, coincubating the antigen-presenting cells with dead or dying cell portions possessing at least one tumor antigen to form loaded antigen-presenting cells, coculturing the loaded antigen-presenting cells with the cytotoxic cell precursors isolated from the patient under conditions for their maturation to form cytotoxic cells, and administering the cytotoxic cells to the patient, wherein the cytotoxic cells express cytotoxic activity against the tumor cells.

In another aspect, the invention is a method of simultaneously administering loaded antigen-presenting cells and tumor specific cytotoxic cells to a patient comprising isolating antigen-presenting cells and cytotoxic cell precursors from the patient, coincubating the antigen-presenting cells with dead or dying cell portions possessing at least one tumor antigen to form loaded antigen-presenting cells, coculturing the loaded antigen-presenting cells with the cytotoxic cell precursors isolated from the patient under conditions for their maturation to form cytotoxic cells; and simultaneously administering the antigen-presenting cells and the cytotoxic cells to the patient.

In another aspect, the invention is a use of cytotoxic cells to elicit tumor rejection, wherein the cytotoxic cells are made according to a process comprising coincubating antigen-presenting cells with dead or dying cell portions possessing at least one antigen to which the immune response is desired to form loaded antigen-presenting cells, coculturing the loaded antigen-presenting cells with naïve T cells under conditions for T cell maturation to form cytotoxic T cells, wherein the cytotoxic T cells express cytotoxic activity against target cells possessing the antigen. The cytotoxic T cells can be CD4 T cells, CD8 T cells or both.

In another aspect, the invention is a use of cytotoxic cells to reduce an immune response, wherein the cytotoxic cells are made according to a process comprising coincubating antigen-presenting cells with dead or dying cell portions possessing at least one antigen to which the immune response is desired to form loaded antigen-presenting cells, coculturing the loaded antigen-presenting cells with naïve T cells under conditions for T cell maturation to form the cytotoxic T cells. The cytotoxic cells can be CD4 positive, CD8 positive or both.

In another aspect, the invention is cytotoxic T cells made according to a process comprising coincubating antigen-presenting cells with dead or dying cell portions possessing at least one antigen to which the immune response is desired to form loaded antigen-presenting cells, coculturing the loaded antigen-presenting cells with naïve T cells under conditions for T cell maturation to form the cytotoxic T cells. The cytotoxic T cells can be CD4 T cells, CD8 T cells or both.

In another aspect, the invention is a method for mounting an immune response mediated by cytotoxic cells comprising coincubating antigen-presenting cells with dead or dying cell portions possessing at least one antigen to which the immune response is desired to form loaded antigen-presenting cells, wherein the dead or dying cell portions are obtained from a first source, coculturing the loaded antigen-presenting cells with cytotoxic cell precursors under conditions for their maturation to form cytotoxic cells, and contacting the cytotoxic cells with target cells possessing the antigen, wherein the target cells are obtained from a second source, wherein the cytotoxic cells express cytotoxic activity against the target cells possessing the antigen. In this method, the target cells can be contacted in vitro or in vivo. The first source can be at least one cell line cultured in vitro or at least one heterologous patient.

In another aspect, the invention is a method for reducing graft rejection of a transplant of donor tissue into a host comprising coincubating antigen-presenting cells with dead or dying cell portions from the donor to form loaded antigen-presenting cells, the dead or dying cell portions possessing antigens to which the reduction of an immune response is desired, administering the loaded antigen-presenting cells into the host at an effective concentration and under conditions for cytotoxic cell precursor maturation into activated cytotoxic cells, and treating the host with a composition to reduce the activated cytotoxic cells prior to transplantation of donor tissue into the host.

In yet another aspect, the invention is a method for reducing graft versus host disease of a transplant of donor tissue into a host comprising coincubating antigen-presenting cells with dead or dying cell portions from the host to form loaded antigen-presenting cells, the dead or dying cell portions possessing antigens to which the reduction of an immune response is desired, administering the loaded antigen-presenting cells into the donor prior to removal of donor tissue at an effective concentration and under conditions for cytotoxic cell precursor maturation into activated cytotoxic cells, and treating the donor with a composition to reduce the activated cytotoxic cells prior to transplantation of the donor tissue into the host.

In yet another aspect, the invention is a method for reducing graft versus host disease of a transplant of donor tissue into a host comprising coincubating antigen-presenting cells with dead or dying cell portions from the host to form loaded antigen-presenting cells, the dead or dying cell portions possessing antigens to which the reduction of an immune response is desired, contacting the donor tissue with the loaded antigen-presenting cells, allowing cytotoxic cell precursors in the donor tissue mature to form cytotoxic cells, and treating the donor tissue with a composition to eliminate the activated cytotoxic cells prior to transplantation of the donor tissue into the host.

In yet another aspect, the invention is a method for inducing antigen-specific tolerance in vivo comprising administering antigen presenting cells loaded with killed cells expressing a desired antigen and treated so as to prevent expression of co-stimulatory molecules but insure antigen presentation.

In yet another aspect, the invention is an in vitro assay to determine the degree of cytotoxic activity of cytotoxic cells against tumor cells from a patient comprising coincubating of antigen-presenting cells with dead or dying cell portions, the dead or dying cell portions possessing antigens to which the immune response is desired, coculturing the loaded antigen-presenting cells with cytotoxic precursor cells under conditions for their maturation into cytotoxic cells, isolating the cytotoxic cells, incubating the cytotoxic cells with the tumor cells, and monitoring the death of the tumor cells, wherein the degree of tumor cell death is proportional to the cytotoxic activity of the cytotoxic cells.

BRIEF DESCRIPTION OF THE DRAWINGS

FIGS. 1A-C depicts that immature DC capture dead or dying tumor cells. In FIG. 1A, DU145 prostate carcinoma cells were induced to apoptosis by anti-Fas (1 µg/ml, CH-11, 16 hr), the generated dead or dying cells were stained with FITC-annexin V and PI. The percentage of dead or dying cells was measured by flow cytometry. In FIG. 1B, DU145 prostate carcinoma cells were induced to apoptosis by anti-Fas (1 µg/ml, CH-11, 16 hr); the generated dead or dying cells were labeled with 7-AAD and incubated with CD1a-FITC labeled immature DC for 1 hr at 37° C. The capture of dead or dying cells by DC was quantitated by flow cytometry as the percentage of CD11a+DC that become positive for 7AAD. Forward scatter/side scatter analysis of CD1a+7-ADD+DC (R1) and CD1a+7-ADD-DC (R2) reveals the increased granularity of the double positive population confirming the engulfment of cell bodies by DC. In FIG. 1C, the immature DC were incubated with dead or dying tumor cells, generated from the indicated tumor cell lines, at either 4° C. or 37° C., and the percentage of double positive cells was measured by flow cytometry assay.

FIGS. 2A-2B depict that monocyte-derived DC (MDDC) from patients with prostate carcinoma efficiently capture PrCa bodies. 7AAD labeled PrCa cell bodies were coincubated with CD1a-labeled monocyte-derived DC, from patient with prostate carcinoma (FIG. 2A) or from healthy volunteers (FIG. 2B), for 1 h at 37° C. Uptake was evaluated by flow cytometry.

FIGS. 3A-3D depict that immature DC loaded with tumor cell bodies induce proliferation of purified CD4+ and CD8+ T cells. CD1a-FITC labeled immature DC were cocultured with dead or dying tumor cells (Ap) for 1 hr at 37° C. and sorted based on CD1a expression. The sorted cells were cocultured for 5 days with autologous purified CD4+ T cells (FIG. 3A) or CD8+ T cells ($5\times10^4$ cells/well) (FIG. 3B). After 4 days of incubation, tritiated thymidine was added, and the thymidine incorporation was measured 16 hr later. The experiments assessing the proliferation of CD8+ T cells were carried out in the presence of CD40L (200 ng/ml) to induce DC maturation and IL-2 (5 U/ml) to enhance T cell proliferation. CD1a-FITC labeled immature DC were cocultured with dead or dying tumor cells (Ap) for 1 hr at 37° C. and sorted based on CD expression. The sorted cells were cocultured for 5 days with autologous purified CD4+ T cells (FIG. 3C) or CD8+ T cells ($5\times10^4$ cells/well) (FIG. 3D) in the presence of mAbs against MHC class I or II molecules before onset of cultures and subsequently during the entire cultures period. After 4 days of incubation, tritiated thymidine was added and the thymidine incorporation was measured 16 hr later.

FIGS. 4A and 4B depict that DC loaded with dead or dying prostate carcinoma cell lines prime CTL. CD1a-FITC labeled immature DC were loaded with prostate carcinoma DU145 (FIG. 4A) or PC3 (FIG. 4B) derived cell bodies for 1 hr at 37° C., sorted based on CD expression and used as stimulator cells. The cultures were set in a 24-well plate by plating stimulator cells with either autologous purified CD8+ T cells or total PBMC. Soluble CD40 ligand (Immunex Corp) was added to induce DC maturation. After 7 days of culture, the T cells were harvested, washed and replated with freshly prepared stimulator cells for 7 additional days. Cytotoxic activity of expanded CTLs was assessed in a standard $^{51}$Cr release assay using sensitizing cells, non-sensitizing cells and K562 as targets. Percent cytotoxicity was measured as a function of spontaneous and total release. Results are representative of three experiments, and each value represents the mean from triplicate wells.

FIG. 9A depicts IFN ELISPOT using as targets DC, either unpulsed or pulsed with the four melanoma peptides (4P). Representative experiment from 3 performed using DC and T cells from different donors. FIG. 9B depicts CTL activity in 4 hour chromium release assay using unpulsed and melanoma-peptide pulsed (4P; mean values of 3 experiments) and control peptide PSA pulsed T2 cells (one experiment).

FIGS. 14A-14C depict the induction of melanoma specific CTL by killed melanoma cells loaded DC using DC and T cells from patient with advanced malignant melanoma. Purified CD8$^+$ T cells are cultured for 3 weeks with unloaded or Me275 loaded DC. FIG. 14A depicts IFN ELISPOT using as targets DC, either unpulsed or pulsed with the four melanoma peptides (4P). Results from one patient. FIG. 14B depicts CTL activity in 4 hour chromium release assay. T cells are able to kill Me275 used for immunization, and the killing is increased when Me275 cells are pulsed with the four melanoma peptides. Similar results were obtained in two patients. FIG. 14C depicts priming of naïve T cells. CD8$^+$CD45RA$^+$ CD45RO$^-$ T cells cultured 3 weeks with DC loaded with killed Me275 cells, kill T2 cells pulsed with 4 melanoma peptides.

DETAILED DESCRIPTION

Figure 1A:
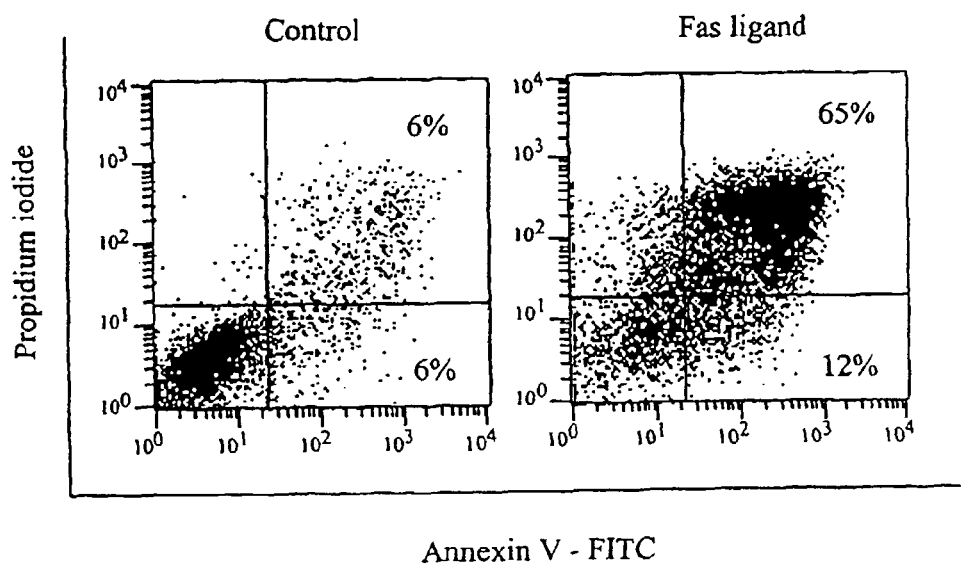

Novel antigen-presenting cells, including but not limited to dendritic cells (DC), that are loaded with antigens from dead or dying allogeneic cell lines, and the methods for making such antigen-presenting cells are described. These loaded antigen-presenting cells are useful to induce both prophylactic immune responses and therapeutic immune responses in humans and animals. In particular, such loaded antigen-presenting cells are useful in the management of cancer and infectious diseases. Alternatively, the loaded antigen-presenting cells can be used to eliminate undesired immune responses such as autoimmune responses and graft versus host disease or host versus graft reaction, i.e., graft rejection in organ and bone marrow transplantation.

Antigen-presenting cells useful in the present invention include but are not limited to dendritic cells at various differentiation stages (precursors, immature dendritic cells and mature dendritic cells), dendritic cells derived from blood precursors including but not limited to monocytes, dendritic cells derived from CD34-hematopoietic progenitor cells, subsets of dendritic cells such as Langerhans cells, interstitial DCs and lymphoid DCs. Preferably the antigen-presenting cells are of human origin. Unless specified otherwise, it is to understood that the terms "dendritic cell" or "DC" as used herein refer to all antigen-presenting cells useful in the present invention. In one embodiment of the present invention, the dendritic cells and responding T cells are derived from healthy volunteers. In another embodiment, the dendritic cells and T cells are derived from patients with cancer or other form of tumor disease. In yet another embodiment, dendritic cells are used for either autologous or allogeneic application.

In the present invention, the novel antigen-presenting cells are obtained by loading dendritic cells with dead or dying allogeneic cells. Dead or dying allogeneic tumor cells useful in the present invention include but are not limited to tumor cell lines and isolated autologous or allogeneic tumor cells. These dendritic cells loaded with dead or dying allogeneic cells are capable of eliciting cytotoxic cells able to kill tumor cells as well as targets loaded with tumor associated antigen derived peptides. The cytotoxic cells include but are not limited to CD8 T cells, CD4 T cells, natural killer cells, and natural killer T cells. It is to be understood hereinafter that unless stated otherwise, reference to cytotoxic T cells means one or more of the cytotoxic cells. Antigen-loaded dendritic cells prepared as described here can also prime naïve T cells to differentiate into effector cells able to recognize multiple and/or shared tumor antigens that are expressed either on the tumor cells that are used to load the dendritic cells and/or on other tumor cells. This cross-priming against multiple antigens shared between different cells, for instance tumor cells is important to elicit broad immune responses. The generation of CTL is associated with MHC class I restricted CD8+ T cell proliferation. The loaded DC can also induce MHC class II restricted CD4+ T cell proliferation This cross-presentation of captured antigens is of particular importance because CD4+ T cells can exert helper function for induction and maintenance of anti-tumor CD8+ T cells, and have a direct effector function against MHC class II positive tumors as well as indirect effector function by activation of other cells, e.g. macrophages.

In the present invention, the CTL elicited by DC loaded with cell bodies from one specific allogeneic tumor source can be used to provide a killing effect on other tumors. For example, CTL elicited by DC loaded with cell bodies derived from a specific allogeneic prostate carcinoma cell line such as PC3 kill other tumor cells lines such as prostate carcinoma DU145 and LnCAP. Similar results have been obtained with melanoma cell lines, breast cancer cell lines, and CTL elicited by DC loaded with LnCAP against PSA peptide-pulsed T2 cells. Thus, an antitumor immune response can be obtained by activation of T cells specific for shared tumor antigens. Moreover, as demonstrated herein, the CTL activity against PSA peptides, using a third prostate cancer cell line, formally proves that 1) the induced CTL activity is not solely due to the existence of shared alloantigens and 2) the presence of alloantigens does not prevent activation of T cells specific for shared tumor antigens.

In the present invention, allogeneic tumor cells can be used for targeting of tumor-associated antigen (TAA) to DC to permit generation of TAA-specific CTL. First, allogeneic cell bodies can be used to load DC to induce anti-tumor responses in patients. These well-characterized antigen sources can permit a more rigorous clinical assessment than the ill-defined autologous tumor preparations that cannot permit standardization and are often limited in their quantity. These shared tumor antigens can be used to generate immune responses that will lead to tumor rejection. An important consequence of the present invention is that the shared tumor antigens do not need to be overexpressed as evidenced with transfected cells or transgenic animals. Finally, this strategy offers the possibility to identify novel shared tumor antigens unavailable from the analysis of T cell clones reacting with autologous tumors.

In the present invention, during the immune responses, alloantigen-specific responses can be eliminated using agents killing activated lymphocytes, (e.g.: anti-Fas antibody) without preventing the development of responses against shared antigens, providing for a method of inactivating autoreactive clones in autoimmune diseases, and allogeneic/xenogeneic specific cell clones in the context of allogeneic/xenogeneic transplantation.

In the present invention, the T cells that are exposed to dendritic cells loaded with killed cells can be tolerized against the antigen(s) expressed on the killed cells. That can be achieved by manipulation of loaded dendritic cells that allows presentation of the antigen but inhibits the expression of co-stimulatory molecules.

Example 1

Induction of an Immune Response Against Prostate Cancer with DC Loaded with Allogeneic Tumor Cell Lines Immature DC Phagocytose Dead or Dying Tumor Cells We determined that in vitro generated immature monocyte-derived DC (MDDC) were capable of capturing dead or dying tumor cells.

Immature monocyte-derived DC were generated from the adherent fraction of peripheral blood monocytes (PBMC) (Bender, et al. 1996. "Improved methods for the generation of dendritic cells from nonproliferating progenitors in human blood," *J Immunol Methods* 196:121). PBMC from a healthy donor were suspended in complete media (CM) consisting of RPMI 1640, 1% L-Glutamine, 1% penicillin/Streptomycin, 50 µM, 2-mercaptoethanol, 1% sodium pyruvate, 1% essential amino acids and heat-inactivated 10% fetal calf serum (FCS) (all from GIBCO BRL, Grand Island, N.Y). The cells were allowed to adhere to plastic dishes (Falcon 6-well plates from Bectin-Dickinson, Franklin Lakes, N.J.). After incubating for 2 hours at 37° C., the nonadherent cells were removed, and the adherent cells were cultured in CM with GM-CSF (100 ng/ml GM-CSF Leukine, Immunex, Seattle, Wash.) and IL-4 (5 ng/ml R & D System, Minneapolis, Minn.). Cultures were fed every 2 days. Cells were routinely used at Day 6, and the DC recovery utilizing this method as determined by immunofluorescence and flow cytometry was >90% of CD1a+CD14-cells, phenotype characteristic of immature monocyte derived DC.

Tumor cell lines Jurkat T cell lymphoma (clone E6-1), prostate carcinomas DU145, PC3, LnCAP, and malignant melanomas A375.S2 and A2058 were purchased from American Type Culture Collection; Manassas, Va. and maintained in CM. The tumor cells were induced to undergo apoptosis. The Jurkat T cell lymphoma and the melanoma cell lines A2058 and A375.S2 were induced to apoptose by treating cells ($1 \times 10^6$/ml) with anti-Fas mAb (1 µg/ml, clone CH-11, from Beckman-Coulter) for 16 hours in CM. This process resulted in approximately >80% of dead or dying cells as determined by annexin V binding and PI staining using a standard methodology well known in the art (FIG. 1A). Before prostate carcinoma PC3 cells were treated with the anti-Fas mAb, they were sensitized with cycloheximide (25

μg/ml, Sigma Chemical Co., St. Louis, Mo.) for 2 hours. The death of the prostate carcinoma LnCAP cells was induced by treatment with TNF-α (40 ng/ml; CellPro, Inc., Bothell, Wash.) for 24 hours followed by γ irradiation (80 Gy).

Prior to culturing the dying tumor cells and DC together, all cells were specifically labeled to detect uptake by the DC of the dying tumor cells. Dying tumor cells were harvested, washed with phosphate buffered saline (PBS) and labeled with the DNA specific fluorescent dye 7-aminoactinomycin (7-AAD) (Sigma Chemical Co.) at 20 μg/ml per $10^6$ cells for 30 minutes at 4° C. The bodies were subsequently washed and resuspended in CM at $1\times10^6$ cells/ml. The immature DC were harvested, washed with staining medium (PBS with 5 mM EDTA and 2% fetal bovine serum (FBS)) and labeled with CD1a-FITC (DAKO, Carpenteria, Calif.) for 45 minutes at 4° C. After staining, DC were washed PBS with 2% FCS (Gibco) and resuspended in CM at a concentration of $2\times10^5$ cells/ml. The DC and dead or dying tumor cells were cocultured at a 1:5 ratio for 1 hour at 4° C. or 37° C. in CM. After coculture, cells were harvested, washed in PBS, and treated with 0.05% trypsin/0.02% EDTA for 5 minutes to disrupt cell-cell binding.

Figure 1C:
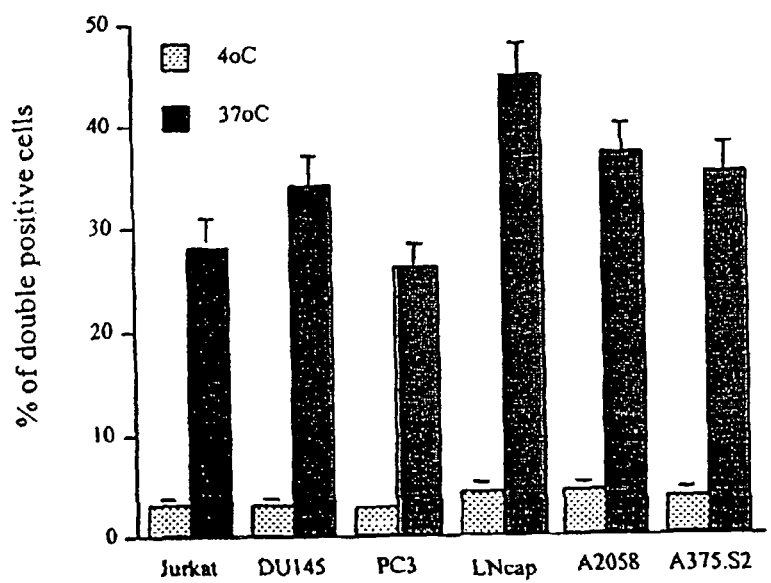

The loading of tumor cell bodies labeled with 7-AAD by FITC-CD1a$^+$ DC was measured by flow cytometry as the percentage of DC doubly positive for FITC-CD1a+ and 7-AAD (FIG. 1B). Forward scatter/side scatter analysis revealed the increased granularity of the double positive population, further confirming the absorption of tumor cell bodies by DC (FIG. 1B). As shown in FIG. 1C, up to 45% of DC were able to load cell bodies of cell lines A2058, A375.S2, DU145, PC3, LnCAP, and Jurkat T lymphoma.

In data not shown, phagocytosis was observed in an autologous setting where dead or dying EBV transformed B-lymphoblastoid cell line or non-transformed B cells were used. The extent to which DC capture dead or dying tumor cells was independent of whether cell death was induced by Fas ligation or by γ-irradiation. DNA staining and a standard Giemsa staining indicated that only a fraction, up to 45%, of the immature DC capture tumor cell bodies containing at least one nuclear fragment. This partial capture did not seem to be due to a lack of substrate as many labeled dead or dying tumor cells remained unengulfed by DC.

Results from fluorescence activated cell sorting and confocal microscopy demonstrated that immature DC have the ability to phagocytose dead or dying cell bodies derived from different tumor cell lines.

DC Derived from Patient with Prostate Carcinoma Capture PrCa Cell Lines

Monocyte-derived DC (MDDC) which were generated by culturing monocytes of a prostate carcinoma patient with GM-CSF and IL-4 were shown to capture bodies derived from PrCa cell lines. Giemsa staining of MDDC indicated that the MDDC had phagocytosed bodies derived from prostate cancer cell line DU145. As shown in FIG. 2A, up to 20% of patient's MDDC phagocytosed DU145 cell bodies, similarly to DC generated from a healthy volunteer (FIG. 2B).

Loaded DC Induce Proliferation of Autologous CD4+ T Cells and CD8+ T Cells

DC loaded with dead or dying allogeneic tumor cells induced proliferation of autologous T cells.

DC were loaded with tumor cell bodies as above and sorted, based on CD1a-FITC staining, to be used as stimulators for autologous T cells. Sources for T cells were unseparated PBMC, purified (>90%) CD4$^+$ T cells and purified (>90%) CD8$^+$ T cells. CD4$^+$ T cells and CD8$^+$ T cells were obtained from Ficoll-separated PBMC of healthy volunteers (with no history of blood transfusion) and depleted of other cells using purified CD3 (UCHT1), CD4 (13B8.2), CD8 (B9.11), CD14 (RMO52), CD16 (3G8), CD19 (J4.119), CD56 (NKH-1), anti-HLA-DR (B8.12.2), and anti-glycophorin A (D2.10) monoclonal antibodies (mAbs) (all from Beckman-Coulter, Miami, Fla.) (Nouri-Shirazi, et al. 2000. "Dendritic cells capture killed tumor cells and present their antigens to elicit tumor-specific immune responses," *J Immunol* 165:3797-3803) and goat anti-mouse IgG Dynabeads (Dynal, Lake Success, N.Y.). The purity of the enriched populations was >85%.

CD1a-labeled DC were cocultured with tumor cell bodies (with no DNA labeling), sorted based on CD1a expression (purity>98%) and plated in round bottom 96-well plates at graded doses from 0 to 5000 DC/well. Autologous PBMC ($1\times10^5$/well/200 μl), purified CD4$^+$ T cells ($5\times10^4$/well/200 μl) or purified CD8$^+$ T ($5\times10^4$/well/200 μl) cells were added to the wells containing CD1a-labeled DC. The proliferation assay was carried out in culture medium supplemented with heat-inactivated 10% human AB serum (Gemini Bio-products, Woodland, Calif.). Soluble CD40L (200 ng/ml, Immunex, Seattle, Wash.) was added at the culture initiation to induce DC maturation, and IL-2 (5 U/ml, Genzyme Co., Cambridge, Mass.) was added to support the proliferation of purified CD8$^+$ T cells. After 4 days of incubation, tritiated thymidine (Wallac, Inc., Gaithersburg, Md.) was added at the activity of 1 μCi/well. The plates were harvested 16 hours later and the incorporated radioactivity was measured by liquid scintigraphy according to manufacturer's instructions.

The same assay to detect T cell expansion was also performed in the presence of mAbs directed against HLA-DR and HLA-A,B,C to determine the antigenic peptides on MHC class I and II molecules presented by DC that are essential for the initiation of T cell proliferation. DC were incubated with mAbs against HLA-DR (clone L243 from Becton Dickinson) and HLA-A,B,C (W 6/32, from DAKO, Botany, N.S.W.) at a final concentration of 5 μg/ml in CM for 30 minutes before the addition of T cells. The mAbs were present throughout the culture period. Irrelevant mAbs were used as isotype controls.

Figure 3C:
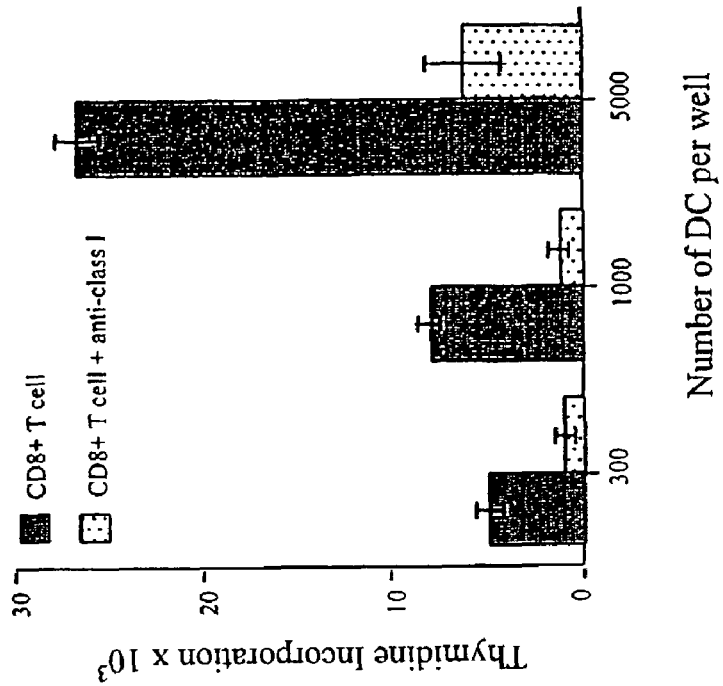
Figure 3D:
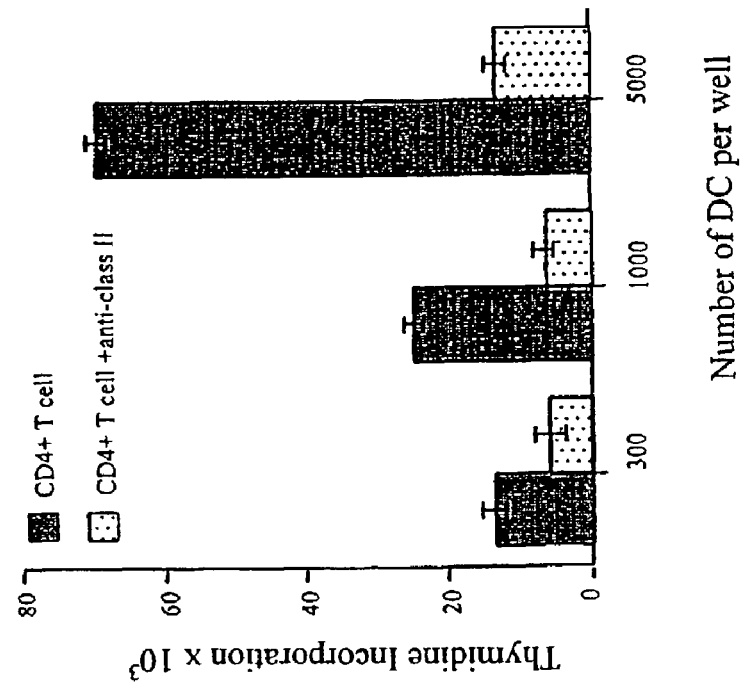

As shown in FIG. 3A, DC loaded with Jurkat lymphoma bodies induced proliferation of autologous CD4$^+$ T cells independently of the presence of exogenous CD40L (which induces DC maturation). As shown in FIG. 3C, CD4$^+$ T cell proliferation was strongly inhibited by the presence of mAbs against class II MHC molecules. Furthermore, DC loaded with DU145 prostate carcinoma cell bodies induced proliferation of autologous CD8$^+$ T cells (FIG. 3B). In data not shown, the induction of DC maturation by the addition of exogenous CD40L and IL-2 was necessary to induce maximal proliferation of purified CD8$^+$ T cells. The inhibition of CD8$^+$ T cell proliferation was also seen when the mAb against class I MHC molecules was added to the cultures (FIG. 3D). Although macrophages were more potent in capturing EBV-transformed cell bodies than immature DC, they failed to elicit CD8$^+$ T cell responses (data not shown).

DC Loaded with Tumor Cell Bodies Lead to CTL Expansion

Once it was demonstrated that DC have the ability to phagocytose dead or dying cell bodies derived from different tumor cell lines and were able to induce proliferation of autologous T cells, it was then determined that DC loaded with tumor cell bodies permits the expansion of CTL possessing cytotoxic activity against the immunizing tumor cell line.

DC loaded with dead or dying tumor cells (as prepared above in this example) were sorted as described above and used as stimulatory cells, while autologous PBMC or purified CD8+ T cells (as prepared above in this example) were used as responders. Cultures were prepared in 24-well plates (Costar, Corning, Inc., Acton, Mass.) by plating 0.5-$1\times10^5$ cells/ ml immature loaded DC with 2×10⁶ cells/ml responder cells in a final volume of 2 ml. Culture medium was supplemented with 10% human AB serum (Gemini Bio-products, Woodland, Calif.) and IL-7 (10 U/ml from Immunex, Seattle, Wash.) in the first seven day cycle. After seven days, cells were harvested and washed in culture medium, and stimulation with tumor loaded DC was repeated for two additional seven days cycles in the presence of IL-2 (10 U/ml, Genzyme Co. Cambridge, Mass.). For each stimulation cycle, a fresh batch of antigen-loaded DC was prepared. The cells were then harvested, and their cytotoxic activity was tested in a standard chromium release assay (Sitkovsky, M. V., *Cytotoxic Cells: Recognition, Effector Function, Generation and Methods*, Henkart, P. A., eds., Birkhauser, Boston, 1993). Cytotoxicity of the T cells sensitized by the DC loaded with antigens from the DU145 prostate carcinoma cell line was compared to the NK-sensitive K562 cell line.

As shown in FIG. 4A, the expanded T cells sensitized by DU145 loaded DC were able to lyse DU145 cells but not the K562 target, thereby demonstrating CTL, rather than NK activity. CTL with equivalent cytotoxic activity were also expanded against the priming tumor cell line when total PBMC, rather than purified CD8+ T cells, were used as responder cells (FIG. 4A). Comparable CTL priming was also obtained when DC were loaded with PC3 prostate carcinoma cell bodies (FIG. 4B). Significantly, the expanded CTL were able to lyse both the PC3 cells used for sensitization and cells from the other prostate carcinoma cell line DU145, substantiating recognition by the CTL of shared antigens. These results showed that these two prostate carcinoma cell lines share antigens able to elicit CTL generation, and demonstrated that DC loaded with tumor bodies allow expansion of CTL with cytotoxic activity against the tumor cell line used for DC loading as well as against shared tumor antigens.

DC Loaded with Prostate Carcinoma LnCAP Cell Bodies Expand PSA-Specific CTL

The loading of DC with tumor cell bodies permitted the induction of c (TAA) specific CTL.

T2 cells, a standard HLA-A201 negative cell line obtained from the American Type Culture Collection, were loaded with PSA specific antigens, using synthetic PSA peptides PSA1 (NH2-FLTPKKLQCV-OH; amino acids 141-150) and PSA2 (NH2-KLQCVDLHV-OH; amino acids 146-154) (Biosynthesis, Lewisville, Tex.). These PSA specific peptides were previously identified as HLA-A2 binding peptides (Correale, et al. 1997. "In vitro generation of human cytotoxic T lymphocytes specific for peptides derived from prostate-specific antigen," *J Natl Cancer Inst* 89:293). HLA-A2 binding affinity of the PSA peptides was evaluated by up-regulation of A2 surface expression on T2 cells after peptide loading. About 1×10⁶ T2 cells were incubated in serum-free complete medium with 50 µg peptide/ml at 37° C. in 5% $CO_2$ overnight. The cells were then washed two times with PBS and subsequently stained with FITC conjugated HLA-A2-specific mAb (10% v/v), HLA-A2, 28 from One Lamda, Inc, Canoga Park, Calif.). The mean fluorescence intensity of HLA-A2 staining with or without peptide loading was analyzed by flow cytometry.

Using methods described previously in this example, DC were loaded with prostate carcinoma cell line LnCAP because these cells express PSA and present PSA peptides in the context of HLA-A2 for T cell-mediated lysis (Correale, et al. 1998. "Generation of human cytolytic T lymphocyte lines directed against prostate-specific antigen (PSA) employing a PSA oligoepitope peptide," *J Immunol* 161:3186). Immunofluorescence staining confirmed the cytoplasmic expression of PSA in LnCAP cells but not in PC3 cells. To assess whether LNCaP bodies loaded in DC were able to elicit HLA-A2-restricted PSA-specific CTL in vitro, immature DC generated from either male or female HLA-A2+ donors were cocultured with LnCAP cell bodies, then sorted and used as stimulators of autologous CD8+ T cells, obtained by methods presented earlier in this example. After three repeated cycles of stimulation, the responder cells were harvested and cytotoxic activity and specificity were determined using LnCAP cells, K562 cells and T2 cells loaded with PSA peptides as targets.

Figure 5:
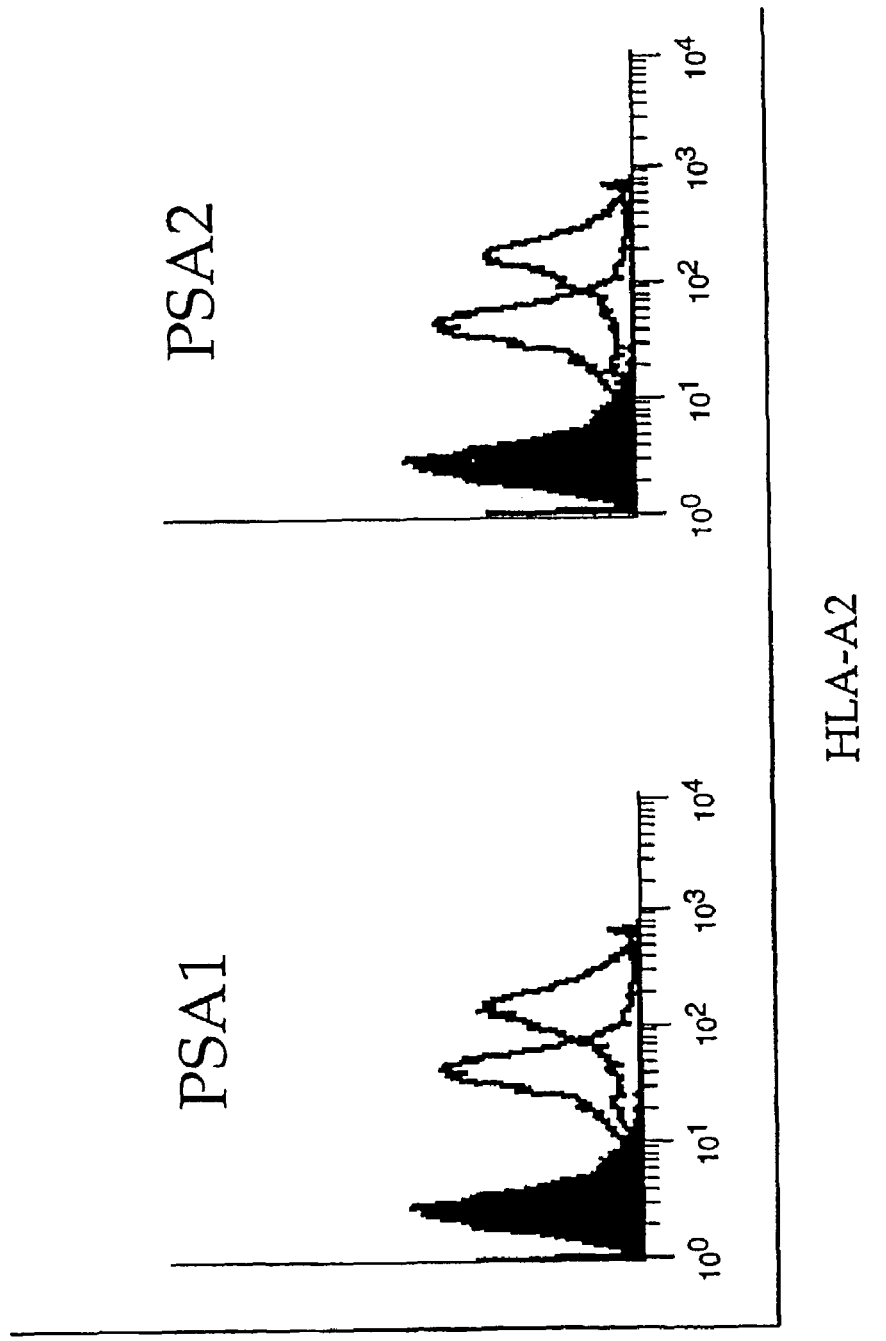
FIG. 5 depicts HLA-A2 binding of PSA peptides, PSA1 and PSA2. T2 cells were incubated with PSA peptides overnight, then the cells were washed and stained with FITC conjugated HLA-A2-specific mAb (HLA-A2, 28). Up-regulation of HLA-A2 molecules on T2 cells after peptide binding was demonstrated as shifted histograms. The filled histograms showed the isotype control staining.
Figure 6B:
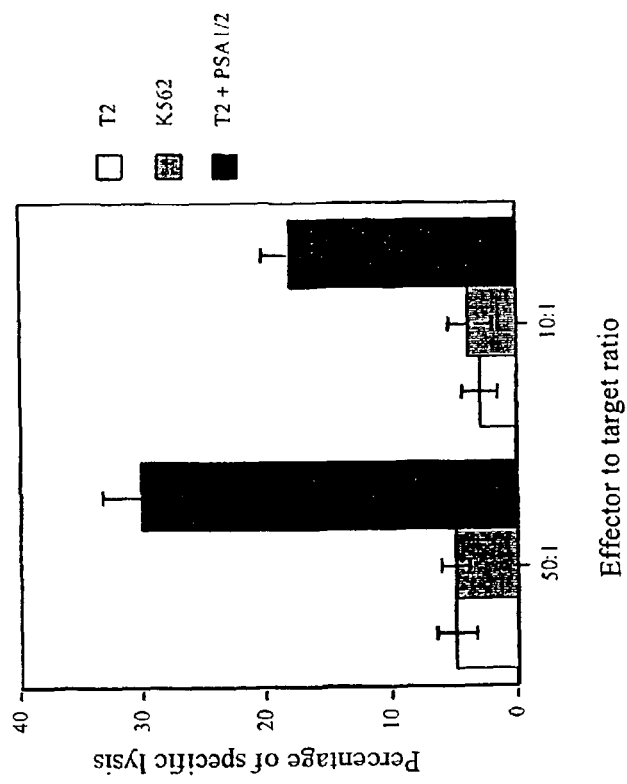
FIGS. 6A and 6B depict DC loaded with dead or dying prostate carcinoma cell line LnCAP induce PSA-specific CTL. CD1a-FITC labeled immature DC, generated from female (FIG. 6A) and male (FIG. 6B) HLA-A2+ donors, were loaded with prostate carcinoma (LnCAP) derived cell bodies for 1 hr at 37° C., sorted based on CD11a expression and used as stimulator cells. The cultures were set in a 24-well plate by plating stimulator cells with autologous purified CD8+ T cells. Soluble CD40 ligand (Immunex Corp) was added to induce DC maturation. After 7 days of culture, the T cells were harvested, washed and replated with freshly prepared stimulator cells for 7 additional days. Cytotoxic activity of expanded CD8+ T cells was assessed in a standard $^{51}$Cr release assay using sensitizing LnCAP cells, T2 cells pulsed with PSA peptides as well as NK-sensitive K562 as targets. Percent cytotoxicity was measured as a function of spontaneous and total release. Results are representative of three experiments, and each value represents the mean from triplicate wells.
Figure 6A:
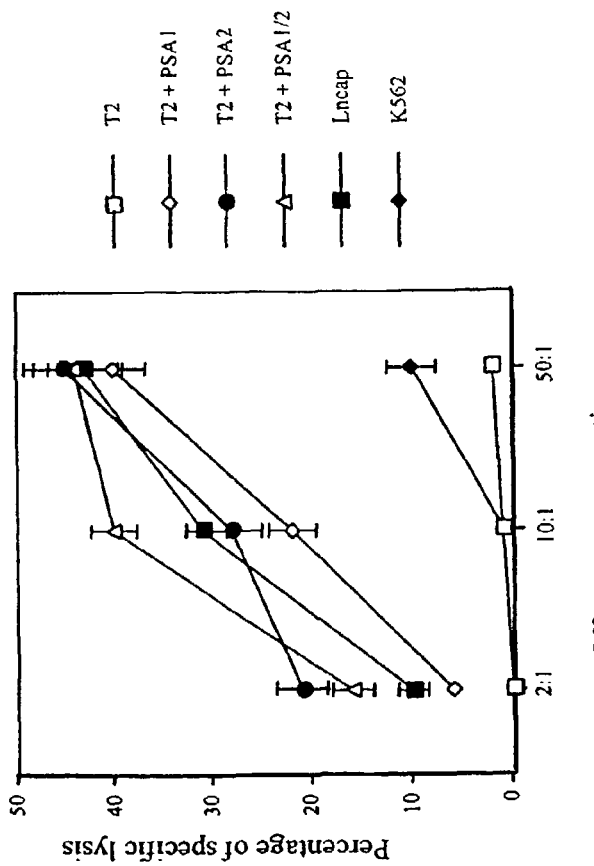

The binding of PSA peptides to T2 cells was confirmed by flow cytometry (FIG. 5). As shown in FIG. 6A, the elicited CTL from a female donor lysed the LnCAP cells but not the NK-sensitive K562 target cells. Importantly, the generated CTL were able to efficiently and specifically kill PSA peptide loaded T2 cells but not unloaded T2 cells. Up to 50% (a five fold increase) of specific lysis of LnCAP cells and PSA-loaded T2 cells was achieved at an effector:target ratio of 50:1, compared to unloaded T2 cells and K562 cells (FIG. 6A). DC generated from a HLA-A2+ male donor were loaded with LnCAP cell bodies and used as stimulators of autologous CD8+ T cells. As shown in FIG. 6B, the CTL generated from a male donor were also able to kill T2 cells loaded with PSA peptides but not unloaded T2 cells nor NK-sensitive K562 cells. In addition, the generated CTL were not able to kill T2 cells loaded with control influenza matrix peptide (MP), again showing the specificity of the response (data not shown).

Example 2

Induction of an Immune Response Against Melanoma with DC Loaded with Allogeneic Tumor Cell Lines DC loaded with killed allogeneic melanoma cells primed naïve T cells to differentiate into CTLs that were specific for a broad spectrum of shared melanoma antigens and were able to kill melanoma cell lines.

Cell Lines and Induction of Tumor Cell Death

The Colo829 and SkMel28 melanoma cell lines, K562, LnCAP prostate carcinoma cell line, 1806 breast cancer cell line (established by Drs. A. Gazdar and J. Minna at UTSW Medical Center at Dallas) and T2 cells were purchased from the American Type Culture Collection (ATCC; Manassas, Va.). The Me275 and Me290 cell lines were established at the Ludwig Cancer Institute in Lausanne. All cell lines were maintained in CM.

ME275 cell death was induced by treatment with 10 µg/ml of betulinic acid for 48 hours. Colo829 cells were killed by the same method, or by gamma irradiation (150 Gy and then cultured 48 hours in serum-free medium). Cell death was assessed by morphology, externalization of phosphatidylserine using FITC-labeled annexin V (CALTAG, Burlingame, Calif.), and staining with DNA specific dyes: 7AAD and trypan blue (Sigma Chemical Co., St. Louis, Mo.).

To determine whether killed allogeneic melanoma cells delivered to DC will permit selection and expansion of T cells specific for shared melanoma antigens two melanoma cell lines were used: Me275 and Colo829. The choice was based on 1) the expression of HLA-A201 by Me275 cells but not by Colo829 cells, and 2) the expression of "known" melanoma TAA, both cell lines expressing Melan A/MART-1, gp100, tyrosinase and MAGE-3 at the RNA and protein level (de Vries, T. J., et al. 1997. "Heterogeneous expression of immunotherapy candidate proteins gp100, MART-1, and tyrosine in human melanoma cell lines and in human melanocytic lesions." *Cancer Res.* 57:3223).

To generate killed tumor cells, several death-inducing factors were tested including DNA damage and receptor-mediated death, cell death being monitored using Annexin V/PI staining. Colo829 cells could be killed by γ-irradiation/serum starvation (150 Gy, >30% of dead cells). Me275 cells proved resistant to γ-irradiation as well as receptor-mediated death via either Fas-ligation, TNF or TRAIL (not shown). However, Me275 cells undergo swift death when treated with Betulinic acid (BA) (Pisha, et al. 1995. "Discovery of betulinic acid as a selective inhibitor of human melanoma that functions by induction of apoptosis," *Nat Med* 1:1046-1051; Fulda, et al. 1999. "Betulinic acid: a new cytotoxic agent against malignant brain-tumor cells," *Int J Cancer* 82:435-441; and Selzer, et al. 2000. "Effects of betulinic acid alone and in combination with irradiation in human melanoma cells," *J Invest Dermatol* 114:935-940). BA is particularly active against melanoma (as well as malignant brain tumor cells) and induces mitochondria-dependent death through activation of caspase-8 and caspase-3. Based on initial kinetic and dose response experiments (not shown) melanoma cells were treated for 48 hours with 10 μg/ml BA (>50% of dead cells, a combination of apoptosis and necrosis). Both Colo829 and Me275 grow as adherent cells and detach when dying, thus the nonadherent fraction composed mostly of killed cells for DC loading was used.

Generation of Monocyte Derived DCs

Immature DC were generated from Ficoll-separated PBMC of HLA-A201$^+$ healthy volunteers or patients with stage IV melanoma. PBMC from nonmobilized or mobilized GM-CSF (Amgen, Thousand Oaks, Calif.) were suspended in CM and allowed to adhere onto plastic dishes (Falcon 6-well, Franklin Lakes, N.J.) for 2 hours at 37° C. The non-adherent cells were removed, and the adherent cells were cultured in CM for 6 days. GM-CSF (100 ng/mL; Leukine, Immunex, Seattle, Wash.) and IL4 (5 ng/mL; Schering-Plough) were added to the culture every two days. The DC recovery at day 7 as determined by a standard immunofluorescence and FACS analysis was >90% of CD1a$^+$ cells. To induce DC maturation, soluble CD40-ligand (sCD40L; 200 ng/mL; Immunex, Seattle, Wash.) was added to the culture from day 5 to day 7.

T Cell Purification

Purified CD4$^+$ and CD8$^+$ T cells (autologous to the DC) were depleted of other cells using purified CD4 (13B8.2), CD8 (B9.11), CD14 (RM052), CD16 (3G8), CD19 (J4,119), anti-CD45 RO (UCHL1), CD56 (NKH-1), anti-HLA-DR (B8.12.2), and anti-glycophorin A (D2.10) monoclonal antibodies (mAbs) (all from IMMUNOTECH, Marseille, France) and goat anti-mouse IgG Dynabeads (Dynal, Lake Success, N.Y.) (Nouri-Shirazi, et al. 2000. "Dendritic cells capture killed tumor cells and present their antigens to elicit tumor-specific immune responses," *J Immunol* 165:3797-3803). For CD8+CD45RA+CD27+ T cells, the CD8+ T cells were stained with anti CD45RA-PE and anti CD27-FITC (Becton-Dickinson Immunocytometry Systems, San Jose, Calif.) and FACS sorted. Purified CD4$^+$ and CD8$^+$ T cells were then used in the T-cell proliferation assay given below.

Flow Cytometry Analysis (FACS)

FACS analysis was performed on a FACSCalibur and sorting on a FACS Vantage (Becton Dickinson, Mountain View, Calif.). Antibodies used to phenotype or sort the cells were Anti-CD1a-FITC labelled (Biosource), Anti-CD14-APC, Anti-CD80-PE, Anti CD83-PE, Anti CD86-PE, Anti-HLA DR-PerCP, Anti CD45RA-PE and Anti-CD27-FITC.

T Cell Proliferation Assay

CD1a-FITC labeled DC were cocultured for 1 hour at 37° C. with tumor bodies, and then sorted based on CD1a expression (purity>95%) and plated in U bottom 96-well plates at graded doses from 0 to 5000 DC/well. Purified CD4$^+$ T cells or purified CD8$^+$ T cells ($10^5$/well/200 μl) were added to plates. The proliferation assay was carried out in culture medium supplemented with heat-inactivated 10% human AB serum (Gemini Bio-products, Woodland, Calif.). Soluble CD-40L (200 ng/ml; Immunex, Seattle, Wash.) was added to induce DC maturation, and IL2 (10 U/ml; Genzyme Co., Cambridge Mass.) was added to support the proliferation of purified CD8$^+$ T cells. After 5 days, tritiated thymidine (NEN, Boston, Mass.) was added at the activity of 1 Ci/well. The plates were harvested 16 hr later (Wallac, Inc., Gaithersburg, Md.) and incorporated radioactivity was measured by liquid scintigraphy according to manufacturer's instructions.

Generation of Specific Cytotoxic T Lymphocytes (CTL)

DC loaded with tumor derived cell bodies and sorted were used as stimulatory cells while autologous purified CD8$^+$ T cells, CD8$^+$CD45RA$^+$CD45RO$^-$ or CD8$^+$CDR45A$^+$CD27$^+$ T cells were used as responders. Cultures were prepared in 24-well plates (Costar) by plating loaded DC at $1 \times 10^5$ cells with $1 \times 10^6$ T cells in a final volume of 1 ml. Culture medium was supplemented with 10% AB serum, sCD40L (200 ng/ml; Immunex, Seattle, Wash.); IL7 (10 UI/ml in the $1^{st}$ week) and IL2 (10 UI/ml in the $2^{nd}$ and $3^{rd}$ week). T cells were restimulated with fresh preparations of unloaded DC or DC loaded with killed tumor cells weekly for two other weeks. Six days after the last stimulation, cells were harvested and their cytotoxic activity as well as the capacity for IFN-γ release were tested.

$^{51}$Cr Cytotoxicity Assay

Cytotoxicity was measured in a standard 4 hours $^{51}$Cr release assay. Briefly, T2 cells were pulsed overnight with 10 μg/ml of the various peptides. Then, the different targets were labeled with $^{51}$Cr (NEN, Boston, Mass.) and washed three times with PBS. Cytotoxic T-lymphocytes (CTL) were co-cultured at 37° C. during 4 hours with $1 \times 10^3$ $^{51}$Cr-labeled target cells in 200 μl of CM supplemented with 10% AB serum in 96-well culture plates. After 4 hours, 50 μl of supernatant was collected and the percentage of killed cells was calculated using the formula: percent release=100×(cpm experiment–cpm spontaneous release)/(cpm maximum release–cpm spontaneous release).

ELISPOT Assay for IFN-γ Release

To quantitate antigen-specific IFN-γ-releasing effector T cells, an enzyme-linked immunospot (ELISPOT) assay was used as recommended by manufacturer. CD8$^+$ T cells (1 to $2 \times 10^5$/well) were added in triplicate to nitrocellulose-bottomed 96-well plates (MAHA S4510; Millipore Corp.) pre-coated with the primary anti-IFN-γ mAb (1-D1K; Mabtech, Sweden) in 50 μl cRPMI per well. For the detection of specific reactive T cells, autologous mature monocyte-derived dendritic cells pulsed with MHC class I-restricted-peptides were added at $10^4$/well (final volume 100 W/well). After 20 hours, wells were washed six times, incubated with biotinylated second mAb to IFN-γ (7 B6-1; Mabtech) for 2 hours, washed and stained with Vectastain Elite kit (Vectors Labs.).

DC Capture Killed Melanoma Cells and Present their Antigens to Autologous T Cells.

The capacity of immature monocyte derived DC to capture killed melanoma cells was evaluated.

Immature DC were mixed with killed melanoma cells at 1:5 ratio and incubated for 1 hour at 37° C. to allow phagocytosis. Thereafter, DC were sorted by flow cytometry based on forward scatter/side scatter properties reflecting size and granularity according to the procedures described herein.

Figures 7A, 7B:
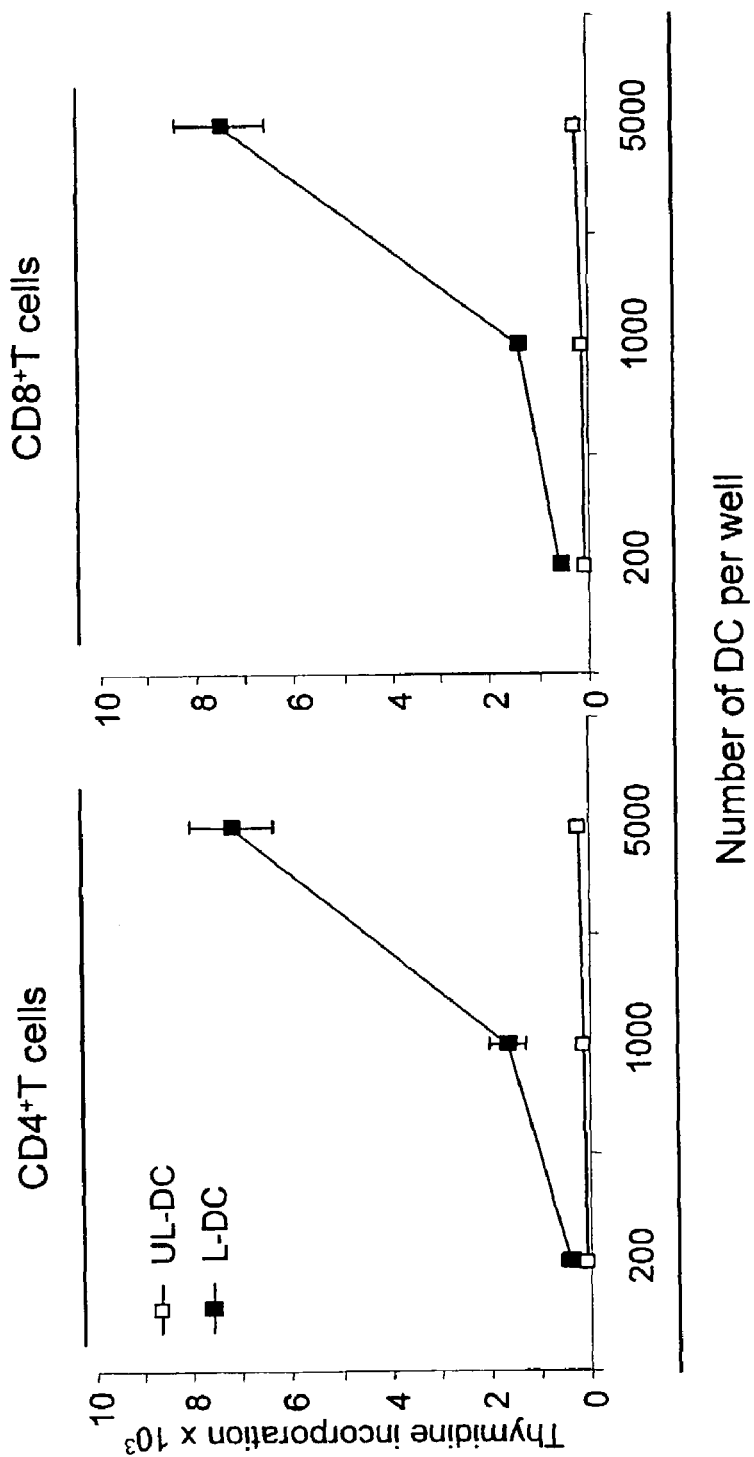
FIGS. 7A and 7B depict DC loaded with killed melanoma cells induce T cell proliferation. Unloaded DC (UL-DC) and loaded DC (L-DC) are sorted and cultured with purified autologous $CD4^+$ (FIG. 7A) and $CD8^+$ T cells (FIG. 7B) (with CD40L and IL2). Thymidine incorporation at day 5. Representative of two experiments.

It was then determined that presentation of loaded antigens by DC could induce proliferation of autologous T cells. As described above in this example, CD1a-FITC labeled immature DC were loaded with killed melanoma cells, sorted by flow cytometry based on CD1a expression (purity>90%) and cocultured with purified (>90%) autologous T cells in the presence of CD40L, which induces maturation of both loaded and unloaded DC as determined by CD83 expression (data not shown). The T cells proliferated when cultured with DC loaded with killed Me275 cells, but not when cultured with killed melanoma cells only (FIG. 7). These results demonstrated that DC captured killed allogeneic melanoma cells and through presentation of their antigens, induced proliferation of autologous T cells.

DC Loaded with Killed Melanoma Cells Elicit CTL Able to Kill Melanoma Cells

It was determined that DC loaded with killed melanoma cells elicit T cells with cytotoxic activity against the melanoma cells used for immunization.

Figure 8A:
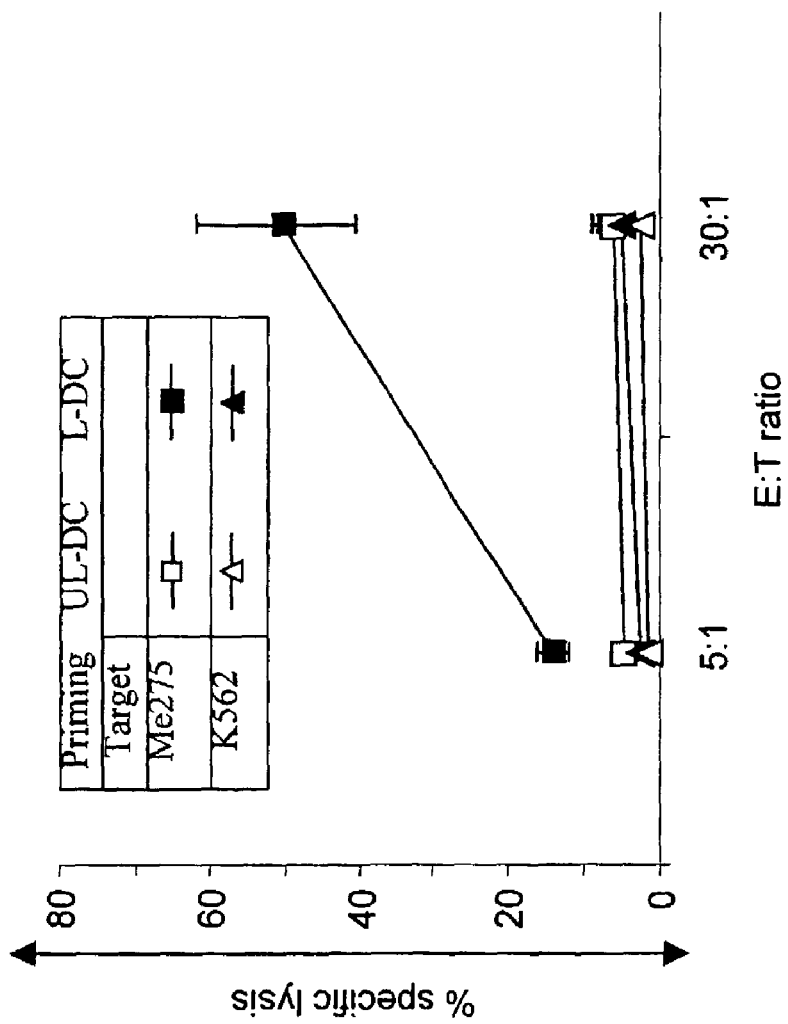
FIGS. 8A and 8B depict the induction of CTL by DC loaded with killed melanoma cells. Purified $CD8^+$ T cells are cultured for 3 weeks with unloaded DC (UL-DC) or DC loaded with Me275. T cells are tested in 4 hour chromium release assay using as targets immunizing Me275 cells and K562 cells as a control for NK activity (a, mean±SE, n=4) (FIG. 8A), as well as unrelated HLA-A201$^+$ tumor cell lines: prostate cancer (LnCAP) and breast cancer (1806) (FIG. 8B). No CTL are elicited when T cells are cultured with killed melanoma cells without the DC (not shown).
Figure 8B:
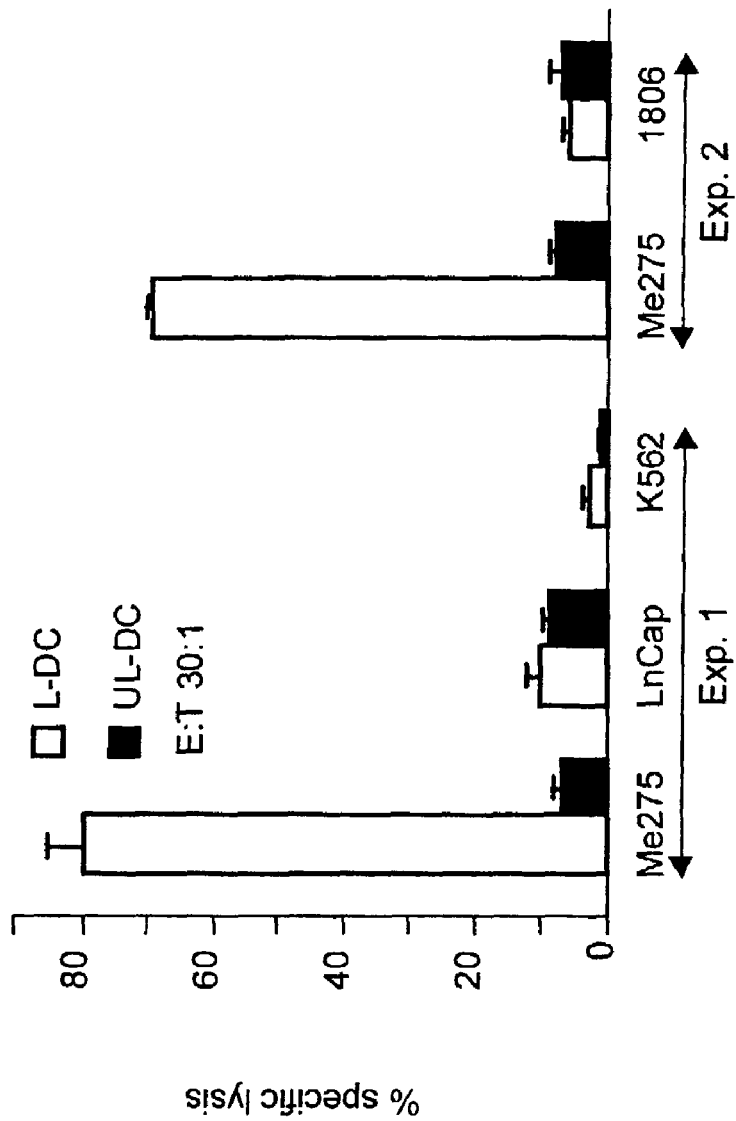

Immature HLA-A201$^+$ DC were loaded with killed Me275, sorted and used to stimulate purified autologous CD8$^+$T cells over a 3-week culture. Soluble CD40L was added to induce DC maturation, as well as IL-7 (10 U/ml 1$^{st}$ week) and IL-2 (10 U/ml in the 2$^{nd}$ and 3$^{rd}$ week) to help T cell proliferation. The T cells were harvested after three stimulation cycles and their cytotoxic activity was determined using Me275, unrelated HLA-A201$^+$ tumor cells, LnCAP, 1806, and NK-sensitive K562 cells. As shown in FIG. 8, loaded DC induced differentiation of CTL able to kill the Me275 melanoma cells, 50±10% specific lysis (mean±SE, n=4; 6±0.5% specific lysis using control T cells cultured with unloaded DC) but neither the unrelated HLA-A201$^+$ tumor cells, LnCAP, 1806, nor NK-sensitive K562 cell line. These results demonstrated that DC loaded with killed allogeneic melanoma cells can trigger CD8$^+$T cells to differentiate into CTL able to kill the melanoma cells used for immunization.

Loading of DC with Killed Allogeneic Melanoma Cells Induced CTL Specific for Multiple Shared Melanoma TAA.

Figure 9A:
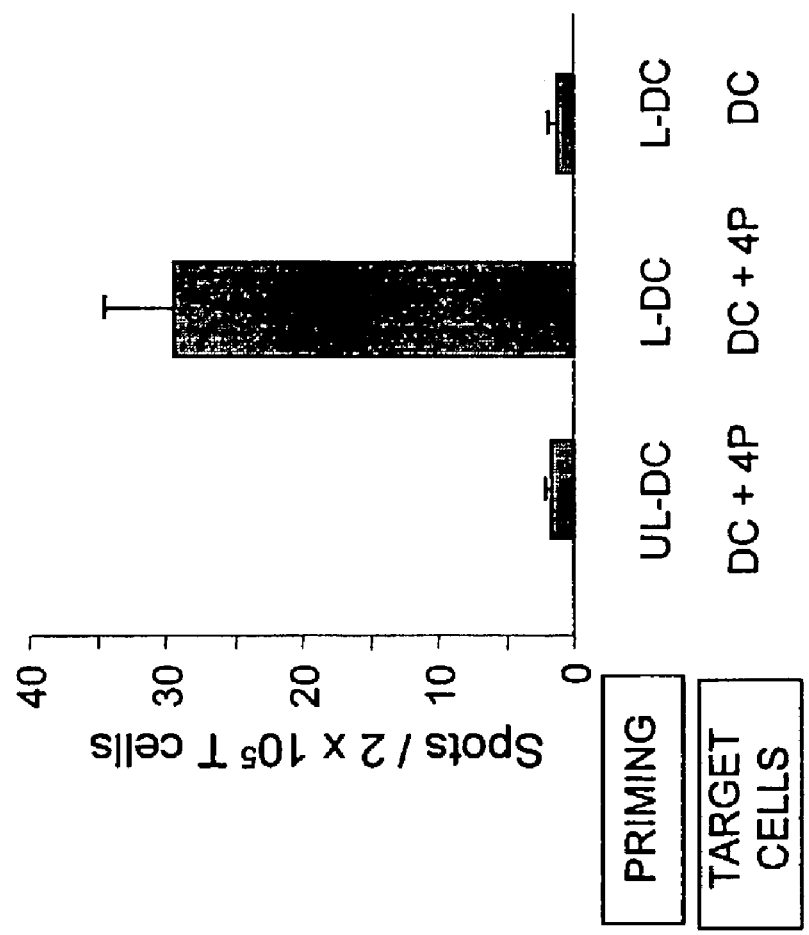
FIGS. 9A and 9B depict the induction of melanoma specific CTL by killed melanoma cells loaded DC. Purified $CD8^+$ T cells are cultured for 3 weeks with unloaded or Me275 loaded DC.
Figure 9B:
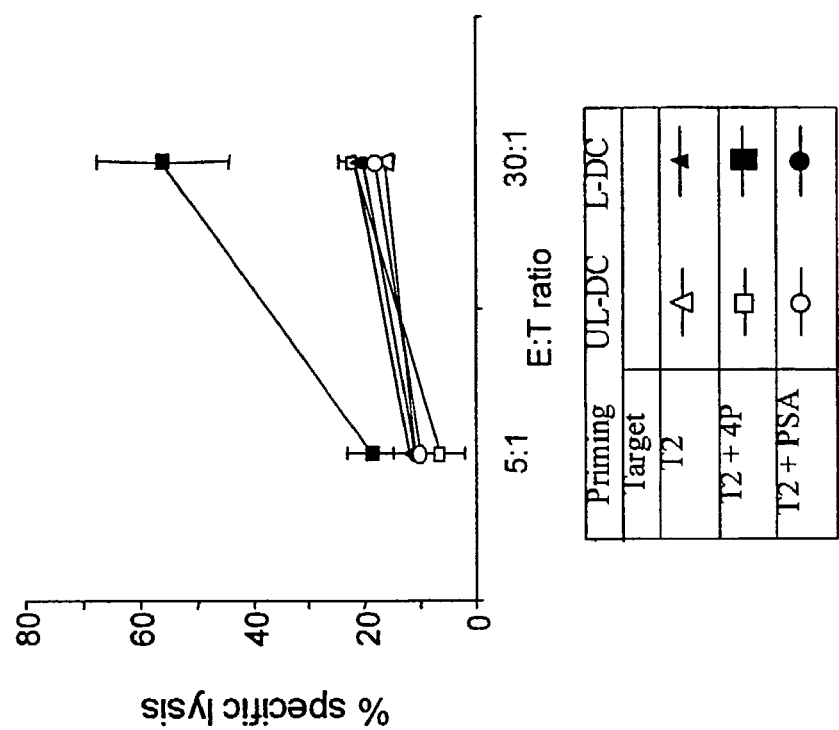

Two assays described above in this example were developed to establish whether the T cell lines generated with killed melanoma cells loaded DC contain T cells specific for melanoma associated antigens: 1) an overnight IFN-γ ELISPOT with the HLA-A201$^+$ DC pulsed with melanoma peptides: Melan A/MART-1$_{27-35}$, tyrosinase$_{368-376}$ and MAGE-3$_{271-279}$ as well as mutated gp100$_{g209-2M}$; and 2) a cytotoxic chromium release assay using T2 cells pulsed with the four peptides as target cells. As shown in FIG. 9A, 3-week CTL lines elicited using DC loaded with killed Me275 cells contain cells recognizing a combination of the four melanoma peptides, 27±2.9 melanoma specific spots/2×10$^5$ T cells (mean±SE, n=3, p=0.03). T cell lines generated with unloaded DC, and peptide-pulsed DC alone (without the T cells) yielded 3±1 and 4±1.5 spots, respectively. As shown in FIG. 9B, these T cell lines were able to kill T2 cells pulsed with a combination of the four peptides (56±13% of specific lysis; mean±SE, n=3), but not T2 cells loaded with a PSA-derived peptide, thus indicating specificity for melanoma TAA. The ability to induce melanoma-specific CTL was not restricted to Me275 cells as the T cells elicited by DC loaded with the HLA-A201$^-$ Colo829 also contained cells that could kill the T2 cells loaded with each of the four melanoma peptides (Table I). Thus, different melanoma cell lines and different methods to kill melanoma cells can be used to load DCs to elicit CTL lines specific for melanoma associated antigens.

TABLE I

T cells elicited by killed melanoma cells loaded DCs kill melanoma-peptide pulsed T2 cells$^a$

|  | No peptide | Tyr | Gp100 | MAGE-3 | MART-1 |
|---|---|---|---|---|---|
| Exp. 1/ Me275 | 18 ± 5$^b$ | 68 ± 5 | 48 ± 4 | nd | nd |
| Exp. 2/ Me275 | 22 ± 2.5 | 60 ± 7 | 40 ± 9.5 | nd | nd |
| Exp. 3/ Colo829 | 19 ± 4.5 | 65 ± 9.5* | 34 ± 3.5* | 33 ± 3* | 36 ± 7.5* |
| Mean SD | 20 ± 2 | 64 ± 4 p = 0.006 | 41 ± 7 p = 0.03 |  |  |

$^a$Percentage of specific lysis, mean of triplicates ± SD. Paired two-tailed t-test on log transformed data comparing the killing of unpulsed and peptide-pulsed T2 cells.
$^b$23% of lysis using PSA peptide-loaded T2 cells.
$^c$p = 0.02;
nd—not done.

DC Loaded with Killed Melanoma Cells Prime Naïve CD8 T Cells to Differentiate into Melanoma Specific CTL It was then determined that DC loaded with killed melanoma cells prime naïve CD8$^+$ T cells to differentiate into melanoma specific CTL.

Figure 10A:
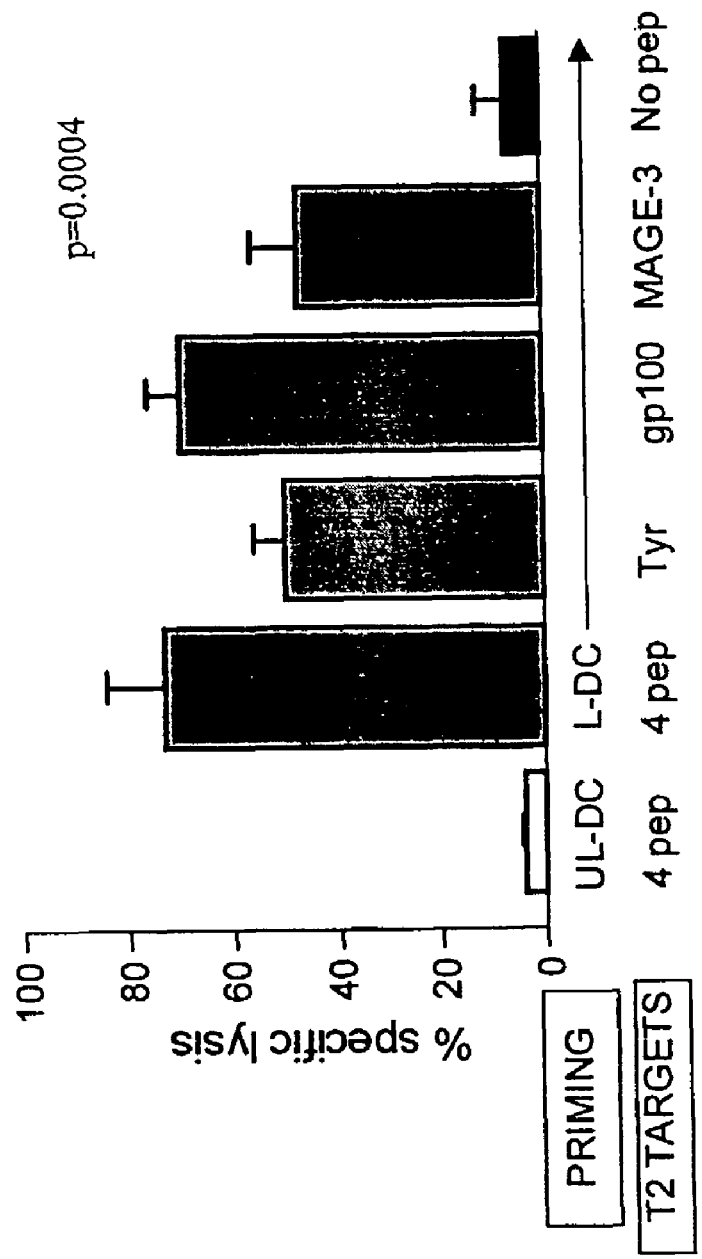
FIGS. 10A-10C depict DC loaded with killed melanoma cells prime naïve T cells. Naïve $CD8^+CD45RA^+CD45RO^-$ T cells are cultured for 3 weeks with unloaded DC (UL-DC) or with DC loaded with killed melanoma cells (L-DC). T cells are tested in a 4 hour chromium release assay. CTL elicited by DC loaded with Me275 bodies kill the T2 cells pulsed with different melanoma peptides (paired two-tailed t-test on log transformed data comparing the killing of unpulsed and peptide-pulsed T2 cells) (FIG. 10A). Naïve $CD27^+CD45RA^+$ $CD8^+$T cells differentiate into CTL able to kill the cell line used for immunization (FIG. 10B) and T2 cells pulsed with melanoma peptides but not PSA peptide (FIG. 10C) (representative of two experiments).

First, CD45RA$^+$CD45RO$^-$ naïve CD8$^+$T cells (>80% pure) were cultured with DC loaded with killed Me275 cells. In two independent experiments, the elicited T cells were able to kill (1) T2 cells pulsed with the four melanoma peptides (up to 70% specific lysis, FIG. 10A), (2) T2 cells loaded with a single peptide: tyrosinase or gp100 or MAGE-3 (FIG. 10A), and (3) the Me275 cell line used for immunization (data not shown).

Figure 10B:
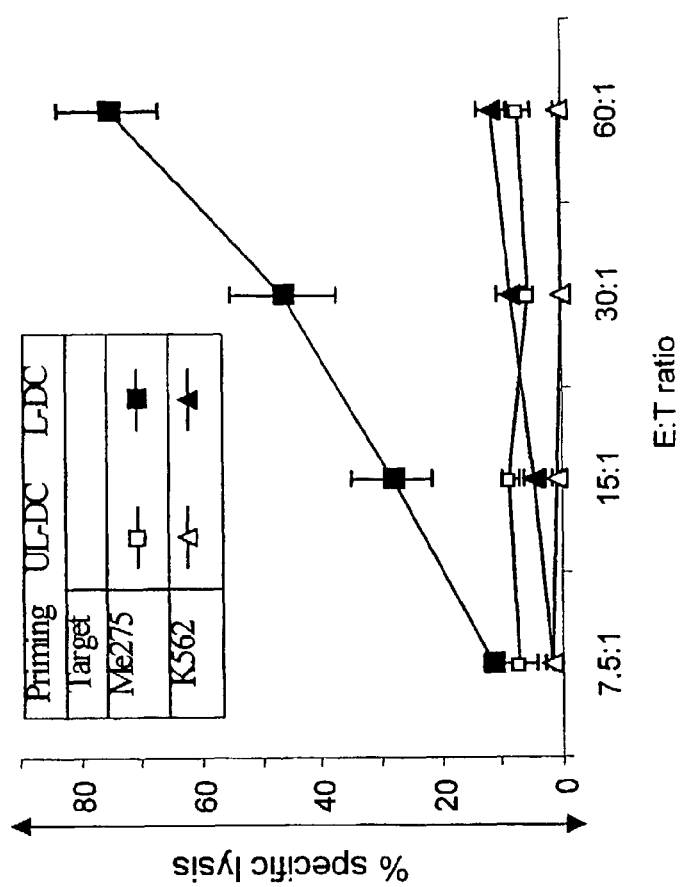
Figure 10C:
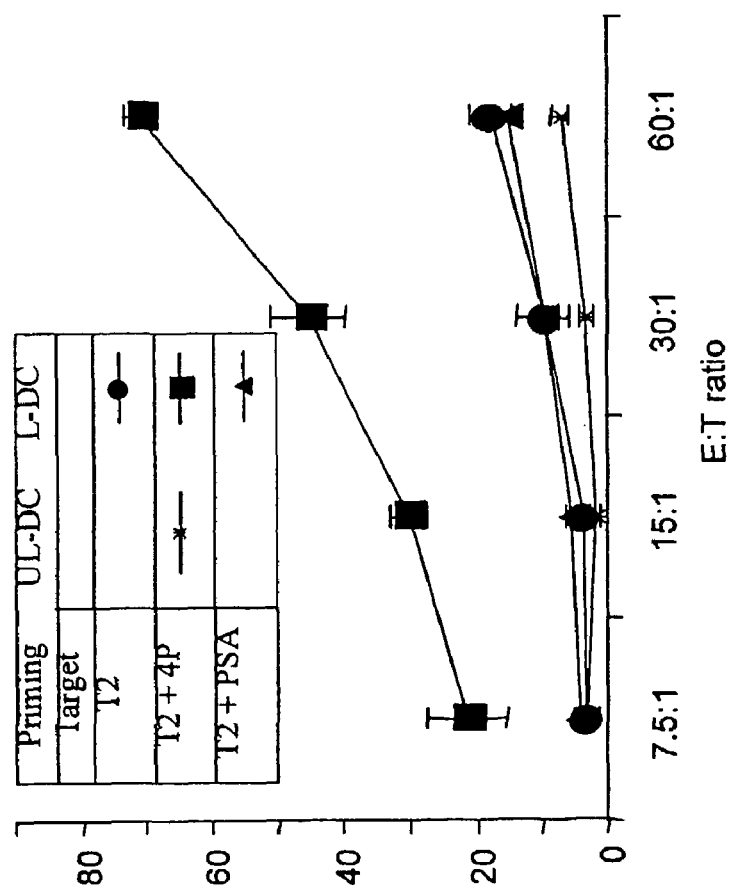
Figure 11:
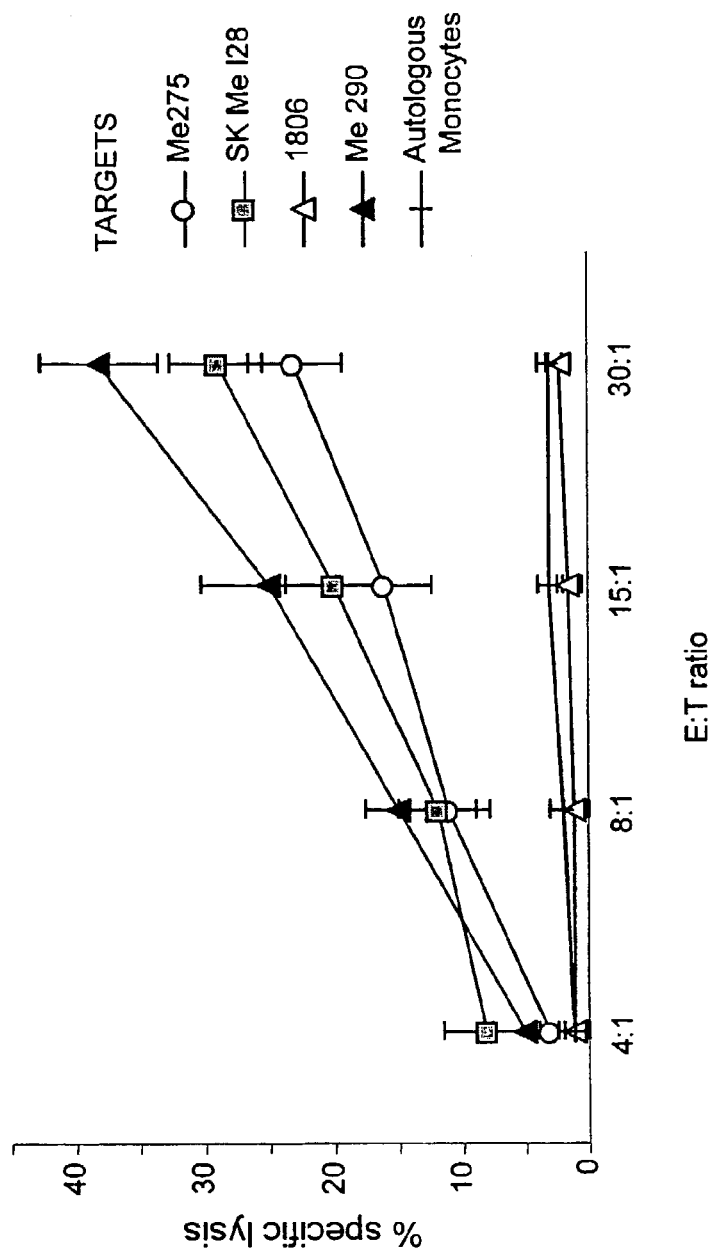
FIG. 11 depicts cross-priming using DC loaded with killed melanoma cells. Naïve $CD27^+CD45RA^+CD8^+$T cells are primed by autologous HLA-A201$^+$DC loaded with killed HLA-A201$^-$ Colo829 cells. The elicited T cells are able to kill HLA-A201$^+$ melanoma targets but neither HLA-A201$^+$ breast cancer cells nor autologous monocytes.

Though mostly comprised of truly naïve T cells, the pool of CD8$^+$CD45RA$^+$CD45RO$^-$ T cells contains a small fraction of "effector memory" cells that might expand in our culture conditions. Therefore, based on CD27 expression, the pool of CD8$^+$CD45RA$^+$CD45RO$^-$ T cells was subdivided to distinguish truly inexperienced T cells (CD45RA$^+$CD27$^+$) from uncommitted effector T cells (CD45RA$^+$CD2T) (Hamaan, D., et al. "Phenotypic and functional separation of memory and effector human CD8+ T cells" 1997. J. Exp. Med. 186: 1407-1418). When cultured with killed melanoma cells loaded DC, these CD8$^+$CD45RA$^+$CD27$^+$ T cells yielded melanoma-specific CTL able to kill both the melanoma cells used for immunization (up to 75% of specific lysis, FIG. 10B) and T2 cells pulsed with melanoma peptides (75% of melanoma-peptide specific killing) (FIG. 10C). The induction of melanoma-specific T cells was further confirmed by IFN-γ ELISPOT with melanoma-peptides pulsed autologous DC (23 peptide-specific spots/10$^5$ T cells versus 5 spots/10$^5$ T cells background, data not shown). Most importantly, these naïve T cells primed by DC loaded with HLA-A201$^-$ Colo829 cells were able to kill HLA-A201$^+$ melanoma targets including Me275, Me290 and SkMel28 cells, thus demonstrating cross-priming (FIG. 11).

Taken together, the results demonstrated for the first time that DC loaded with killed allogeneic melanoma cells can prime naïve CD8$^+$ T cells to differentiate into CTL specific for shared melanoma associated antigens and were able to kill tumor cells HLA matched to the dendritic cells.

Figure 12A:
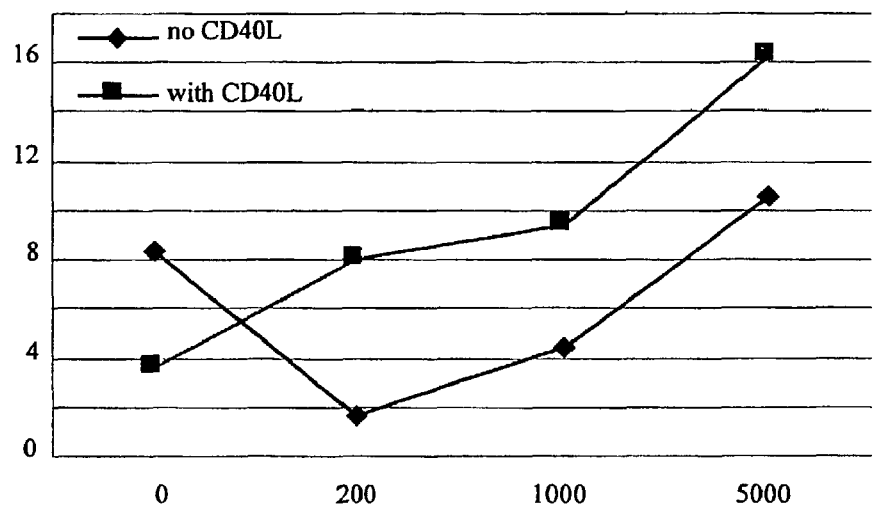
FIGS. 12A and 12B depict that CD34+HPC-derived DC subsets in stage IV melanoma capture dead or dying melanoma cells and induce proliferation of autologous T cells. CD34+HPC were cultured for 9 days with GM-CSF, TNF and FLT3L. Total DC (FIG. 12A) and their isolated subsets (FIG. 12B) were then loaded with dead or dying melanoma cell line COLO829. After overnight culture in the presence of DC maturation factor CD40L, DC were subsequently cultured at graded doses (horizontal axis) with autologous T cells for 5 days. T cell proliferation was determined by thymidine uptake (vertical axis, ×10$^3$).
Figure 12B:
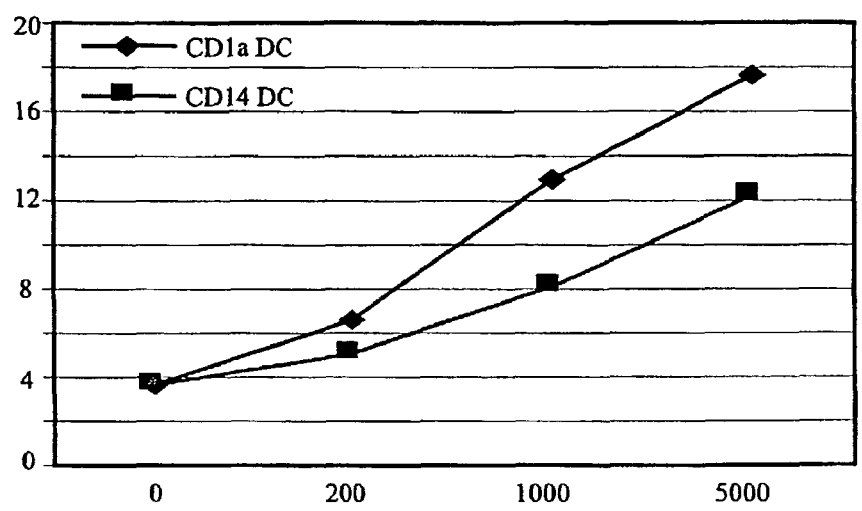
Figure 13A:
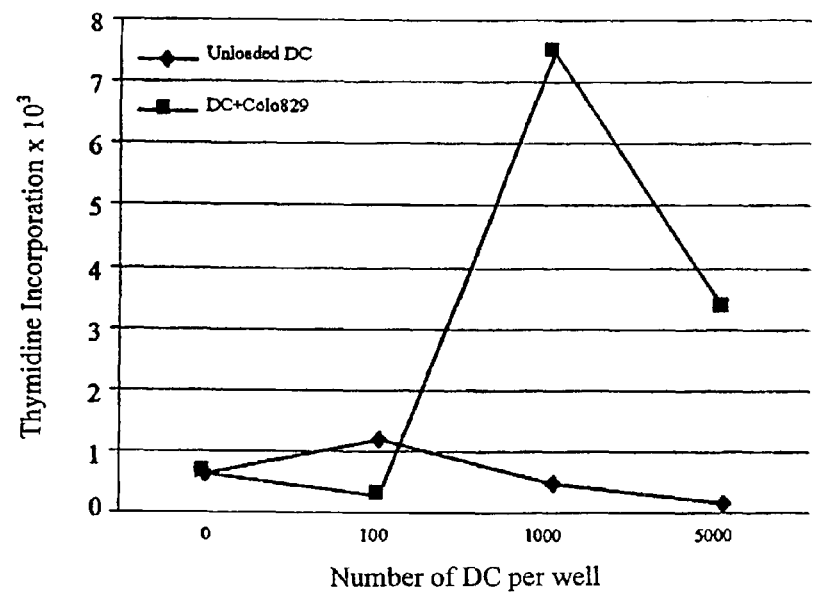
FIGS. 13A and 13B depict that immature DC from melanoma patient capture dead or dying melanoma cells and induce proliferation of both CD4+ and CD8+ T cells. Immature DC from patient with stage IV melanoma were cocultured with melanoma bodies for 1 hr, sorted and cocultured for 5 days with autologous purified CD4+ T cells (+CD40L) (FIG. 13A) or CD8+ T cells (5×10$^4$ cells/well) (FIG. 13B) and tritiated thymidine was measured at Day 5 (vertical axis× 10$^3$). The proliferation of CD8+ T cells was carried out in the presence of CD40L (200 ng/ml) and IL-2 (5 U/ml).
Figure 13B:
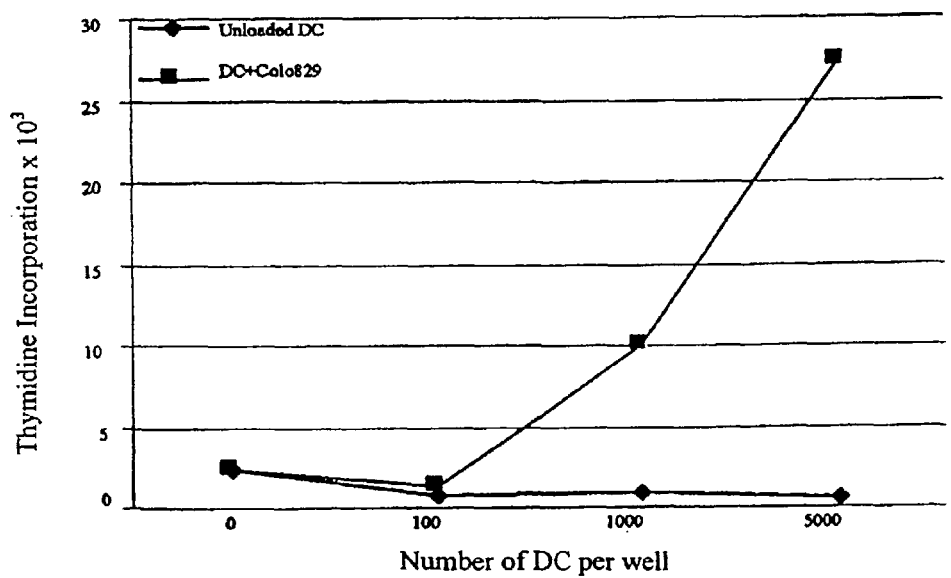

DC Obtained from Patients with Stage IV Melanoma Capture Dead or Dying Melanoma Cells and Induce Proliferation of Autologous T Cells In another phase of the study, the capacity of DC derived from blood CD34+HPC in stage IV melanoma patients to capture dead or dying melanoma cells and to present their antigens to autologous T cells was measured. To this end, CD34DC at Day 9 of culture were sorted based on CD1a and CD14 expression. The total CD34DC and their isolated subsets were cultured with allogeneic melanoma cell line COLO829 cells induced to die by γ-irradiation for 4 hours to allow antigen capture and subsequently overnight with CD40L to allow DC activation/maturation. Thereafter, DC were used as stimulators in culture with autologous T cells. As shown in FIGS. 12A and 12B, only mature CD34DC loaded with dead or dying melanoma cells induced proliferation of autologous T cells. Furthermore, while both subsets were capable of antigen capture and presentation in this system, CD1a DC seem more efficient in inducing proliferation of autologous T cells. These data indicate that CD34+HPC-derived dendritic cells, which consists of Langerhans cells and interstitial DC, can capture and present allogeneic tumor cell bodies. FIGS. 13A and 13B demonstrates immature monocyte-derived DC from a patient with stage IV melanoma cocultured with dead or dying cells from a melanoma cell line induce proliferation of both autologous CD4+ T cells (FIG. 13A) and CD8+ T cells (FIG. 13B).

DC Loaded with Killed Melanoma Cells Elicited Melanoma Specific Responses from Blood T Cells of Patients with Stage IV Melanoma.

Although it would be desirable to vaccinate melanoma patients with DC loaded with killed melanoma cells to elicit immune responses, these patients could suffer from immune dysfunction that may be reflected in the inability of their blood T cells to mount melanoma-specific immune responses (Lee, P. P., et al. "Characterization of circulating T cells specific for tumor-associated antigens in melanoma patients" 1999. *Nat. Med.* 5:677-685). It was found that the DC loaded with killed allogeneic melanoma cell lines can elicit melanoma-specific CTL using blood T cells and DCs from patients with advanced malignant melanoma.

Figure 14B:
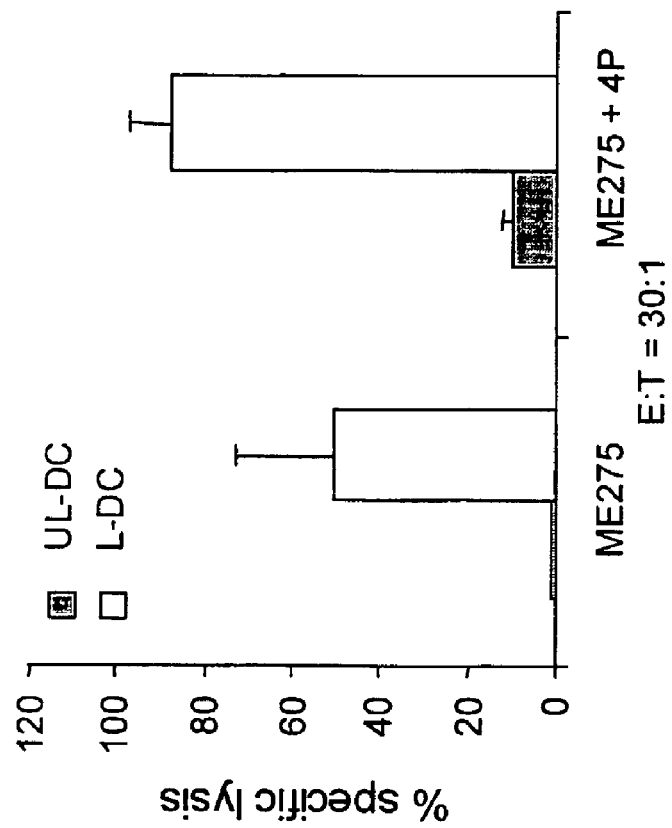
Figure 14C:
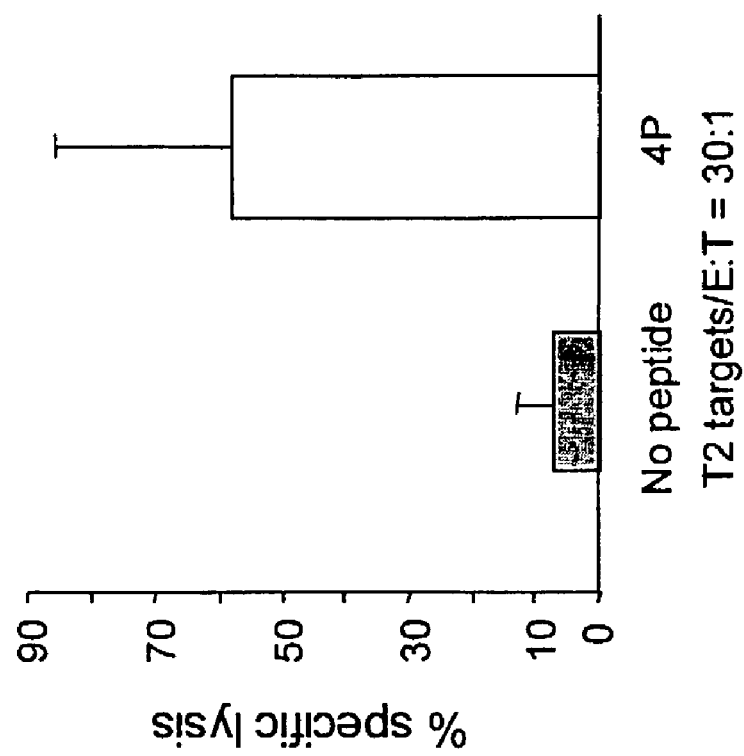

To determine whether CD8+ T cells from patients with metastatic melanoma could be differentiated into effective melanoma specific CTL, purified CD8+T cells cultured for 3 weeks with DC loaded with killed Me275 cells contain melanoma-specific T cells as determined by IFN-γ ELISPOT using peptide-pulsed DCs (15 spots/2×10$^5$ T cells, patient #6, FIG. 14A). As shown in FIG. 14B, purified CD8+T cells cultured with killed Me275 loaded DC generated CTL lines able to kill Me275 cells, either unpulsed (50% specific lysis) or pulsed with the four melanoma peptides (88% specific lysis; patient #1). In two patients, CD45RA+CD45RO− CD8+T cells cultured for three weeks with killed melanoma cells loaded DC, were found to differentiate into melanoma-specific CTL as shown by their capacity to kill T2 cells pulsed with a combination of four melanoma peptides (FIG. 14C and data not shown).

Example 3

Figure 15:
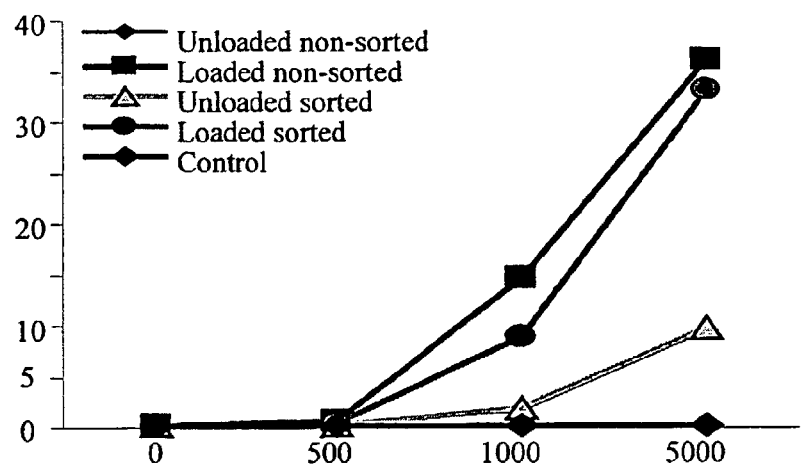
FIG. 15 depicts that DC loaded with killed breast cancer cells induce proliferation of autologous CD4$^+$ T cells. Loaded DC are prepared and cultured at graded does with 10$^5$ autologous CD4$^+$ T cells (purity>85%). T cell proliferation is determined after 5 days by thymidine incorporation (cpm×10$^3$). The control curve represents cpm from wells where killed BrCa cells were plated together with the T cells.

Induction of an Immune Response Against Breast Cancer with DC Loaded with Allogeneic Breast Cancer Cell Lines It has now been found that DC loaded with killed breast cancer cells can induce proliferation of autologous CD4 T cells. DC were first loaded with killed breast cancer cells, either sorted or enriched by differential centrifugation, and then cocultured at graded doses with 1×10$^5$ autologous CD4 T cells (purity>85%). Monocyte-derived DC and T cells were prepared as described in the Examples 1 and 2. Capture of killed breast cancer cells by immature DC was monitored by flow cytometry and Giemsa staining as described in the Examples 1 and 2. After 5 days of co-culture with T cells, tritiated thymidine (NEN, Boston, Mass.) was added to each well at the activity of 1 Ci/well. The plates were harvested 16 hours later (Wallac, Inc., Gaithersburg, Md.) and incorporated radioactivity was measured as described above. As shown in FIG. 15, the loaded DC induced T cells from healthy volunteers to proliferate, indicating that DC can process antigens from killed breast cancer cells and present them to autologous CD4+ T cells.

It was also determined that different tumor cells may require unique conditions for loading DCs with killed tumor cells. The method for DC loading that yielded sufficient antigen presentation when killed melanoma cell lines or prostate cancer cell lines were used, was not sufficient when killed breast cancer cells were used. Thus, a new method was established where DCs are co-cultured with killed breast cancer cells, at the 1:1 ration, for 48 hours.

Figure 16:
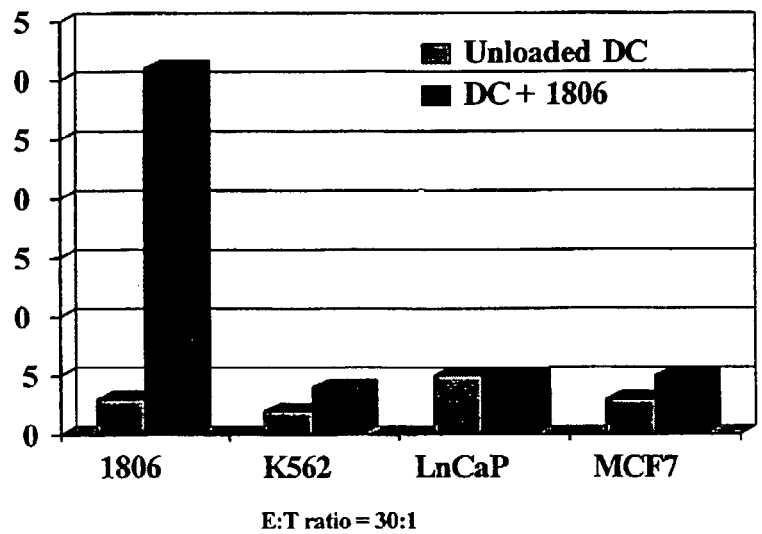
FIG. 16 depicts loaded DC can sensitize T cells which in turn can kill specific tumor cells. Immature DC are mixed with killed allogeneic breast cancer cells 1806. The DC are incubated with killed tumor cells for 48 hours in the presence of monocyte conditioned medium to induce DC maturation. Harvested DC are then used as stimulators of autologous CD8 T cells in 3-weeks cultures (3 stimulations). Harvested T cells are tested in a chromium release assay (percentage specific lysis, vertical axis).

It was also determined that T cell lines having cytotoxic activity against breast cancer can be generated in vitro. Immature DC were mixed with killed allogeneic breast cancer 1806 cells (killed by a combination of CHX and Fas ligation as described in the Example 1), cultured for 48 hours at 1:1 ratio in the presence of cytokines inducing DC maturation TNF-a (10 ng/mL), IL-6 (10 ng/mL) and IL-1 (10 ng/mL) (all from Genzyme). Thereafter, the DC were used to stimulate purified autologous CD8 T cells using the procedures described in the Examples 1 and 2. The T cells were harvested using a chromium release assay after three stimulation cycles, and their cytotoxic activity was determined using a panel of tumor cell lines. As shown in FIG. 16, DC loaded with breast cancer 1806 bodies induced differentiation of CTL able to kill 1806 breast cancer cells with 30% of specific lysis but not the NK-sensitive K562 cell line nor other tumor cells, LnCaP and MCF-7.

Figure 17:
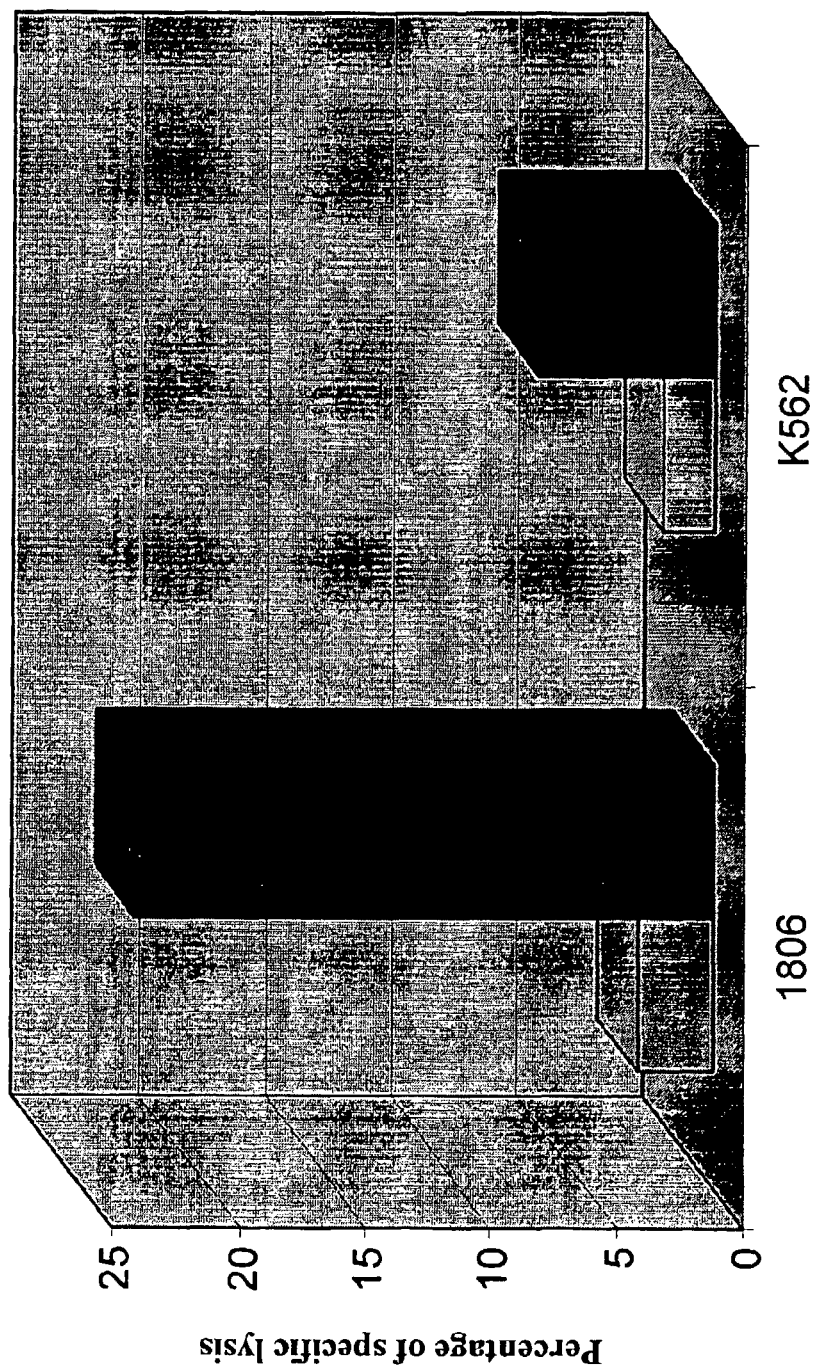
FIG. 17 depicts mature loaded DC can sensitize T cells to kill tumor cells. Immature DC are mixed with killed allogeneic breast cancer cells 1806. The DC are incubated with killed tumor cells for 48 hours in the presence of monocyte conditioned medium to induce DC maturation. Harvested DC are then used as stimulators of autologous peripheral blood lymphocytes in 3-weeks cultures (3 stimulations). Harvested T cells are tested in a chromium release assay (percentage specific lysis, vertical axis).

It was also determined that DC loaded with killed breast cancer cells can elicit cytotoxic T cells when cultured with the peripheral blood lymphocytes, without the need for T cell purification and without adding cytokines to help T cell proliferation (such as IL-2 and IL-7). All procedures are the same as above except that peripheral blood lymphocytes are used instead of purified CD8 T cells (FIG. 17).

Figure 18:
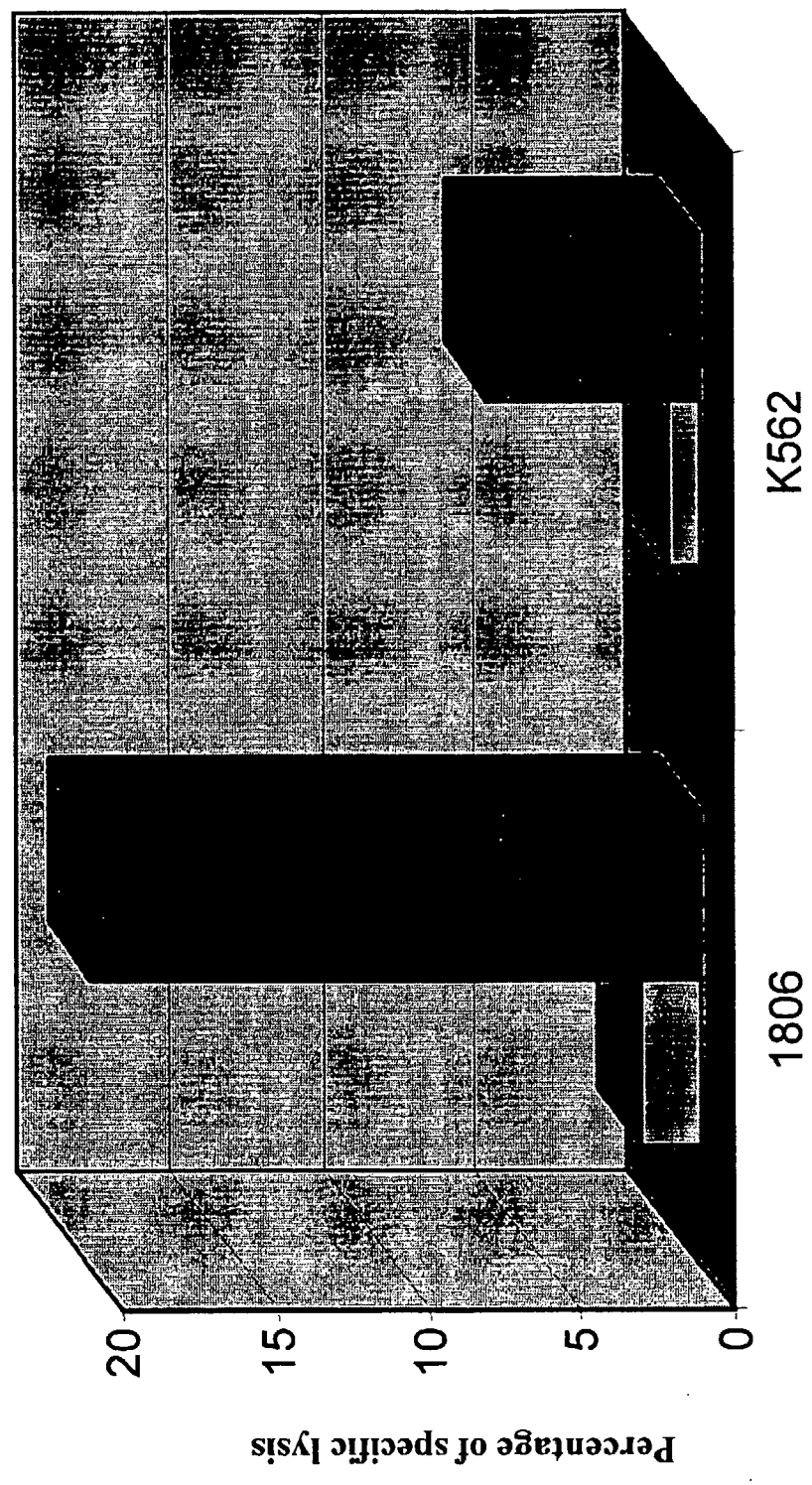
FIG. 18 depicts loaded DC can sensitize T cells to kill tumor cells without the need for exogenous DC maturation factors. Immature DC are mixed with killed allogeneic breast cancer cells 1806. The DC are incubated with killed tumor cells for 48 hours. Harvested DC are then used as stimulators of autologous peripheral blood lymphocytes in 3-weeks cultures (3 stimulations). Harvested T cells are tested in a chromium release assay (percentage specific lysis, vertical axis).

It was also determined that breast cancer specific CTL can be elicited by DC loaded with killed breast cancer cells using peripheral blood lymphocytes without adding cytokines to induce DC maturation during loading with killed breast cancer cells. Thus, the immature DCs are mixed with killed breast cancer cells (all procedures as above) and cultured for 48 hours in CM. Thereafter the loaded DCs are used as stimulators of autologous peripheral blood lymphocytes. All procedures are the same as above (FIG. 18).

Figure 19:
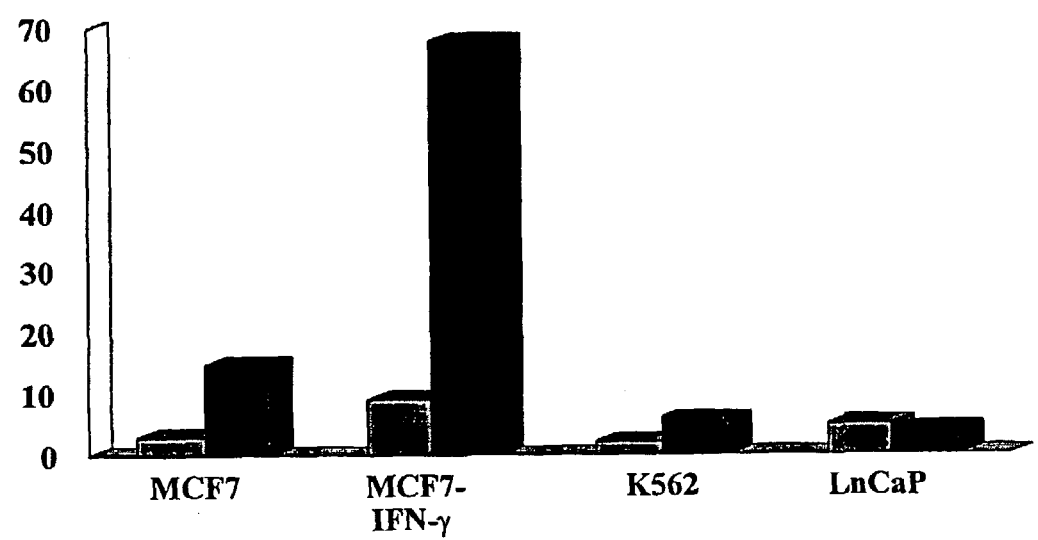
FIG. 19 depicts loaded DC can sensitize T cells which in turn can kill specific tumor cells. Immature DC are mixed with killed allogeneic breast cancer cells MCF. The DC are incubated with killed tumor cells for 48 hours in the presence of monocyte conditioned medium to induce DC maturation. Harvested DC are then used as stimulators of autologous CD8 T cells in 3-weeks cultures (3 stimulations). Harvested T cells are tested in a chromium release assay (percentage specific lysis, vertical axis). MCF-7 cells are incubated with IFN-γ for 7 days prior to use as CTL targets.

It was also determined that treatment of tumor cells with IFN-γ increased both the immunogenicity of killed tumor cells (not shown) as well as their susceptibility to CTL mediated lysis (FIG. 19). All procedures are the same as above except that that breast cancer cells are treated with IFN-γ for 1 week before being used as targets in the cytotoxicity assay. By this method, breast cancer-specific CTLs can be elicited using different breast cancer lines (data not shown), indicating that DC loaded with dead or dying breast cancer cells can be used in immunizing people against breast cancer.

Example 4

DC Loaded with Allogeneic Cell Lines can be Used to Eliminate Unwanted Immune Responses Because allogeneic tumor cell lines were used as a source of tumor antigens, the response to alloantigens could represent a major component of the induced CTL responses.

Therefore, an in vitro system was found to allow for the elimination of allo-specific T cells and potential enrichment of tumor antigen specific CTL. The melanoma cell line COLO829 was the source of both alloantigens and tumor associated antigens, while the EBV transformed cell line (COLO829-BL) derived from the same donor was the source of alloantigen.

Figure 20:
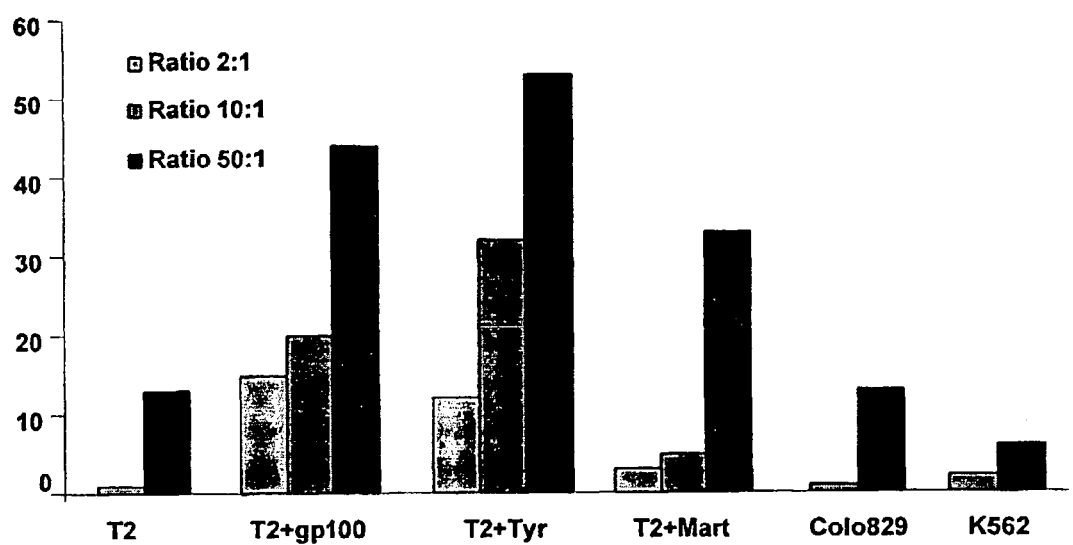
FIG. 20 depicts that tumor antigen specific CTL can be enriched by elimination of allo-specific T cells. The graph depicts the percentage of specific lysis (ordinate axis) of peptide loaded T2 cells and K562 cells at indicated effector to target ratios. Effector cells were generated from adult CD8+ T cells, after elimination of allo-specific T cells by two rounds of stimulation (7 days each) with autologous DC loaded with COLO829 derived bodies in the presence of IL-7 (10 U/ml, first cycle) and IL-2 (10 U/ml, 3rd and 4th cycle). CD40 ligand was added to induce DC maturation. T2 cells were loaded with peptide for 2 hours.

DC were loaded with COLO829 bodies, sorted as described above and used as stimulators for autologous CD8$^+$T cell expansion plated in a 1:5 ratio. T cells were primed in the first cycle using the same procedure as described in Example 1 by COLO829 loaded DC, harvested and subsequently cocultured, in a second cycle, with DC loaded with the EBV transformed cell line COLO829-BL in the presence of exogenous Fas-ligand anti-Fas antibody as described in Example 1 (Immunotech, Marseille, France). The concept behind this approach was that the use of EBV cell bodies and Fas ligand allows elimination of allo-responsive T cells. After these two seven day cycles, the surviving CD8$^+$T cells were harvested and restimulated in two more seven day cycles by DC loaded with COLO829 melanoma cell bodies to expand the melanoma-antigen specific T cells. The resulting cytotoxic activity was determined in the standard $^{51}$Cr release assay using melanoma peptides loaded in T2 cells and the NK-sensitive K562 cells as targets (same methods as described above). As shown in FIG. 20, the elicited CTL line was able to specifically lyse T2 cells loaded with gp100, tyrosinase and to a lesser extent with MART-1 peptides. Thus, tumor antigen specific CTL can be enriched by elimination of allo-specific T cells. These results indicated cross-presentation of the tumor antigens and feasibility of the elimination of allo-specific CTL and provided the rationale and tools for immunization of prostate carcinoma patients with DC loaded with bodies of allogeneic prostate carcinoma cell lines, and identification of novel, shared, prostate tumor associated antigens.

Example 5

Figure 21:
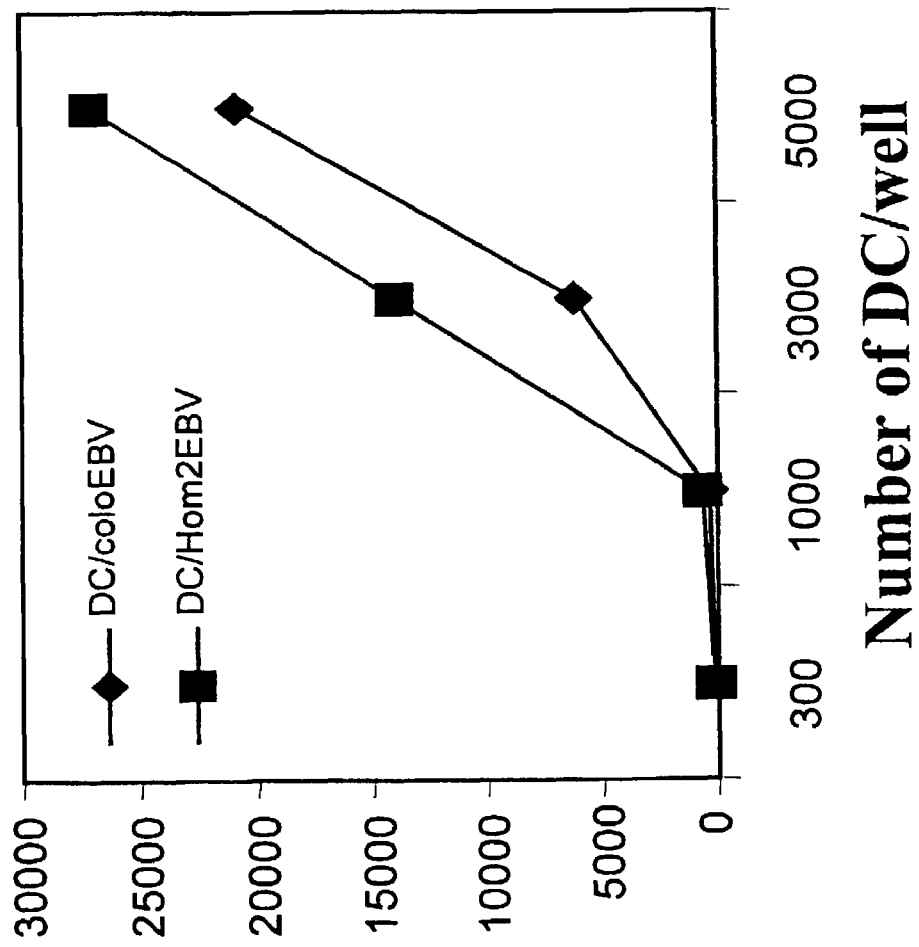
FIG. 21 depicts DC loaded with killed EBV cell lines induce proliferation of naïve CD4 T cells. Immature monocyte-derived DC are loaded with killed EBV cells, sorted based on CD11a expression and cultured for 5 days with autologous naïve CD4+CD45RA+ T cells. Proliferation is measured by thymidine incorporation (cpm, vertical axis).
Figures 22A, 22B:
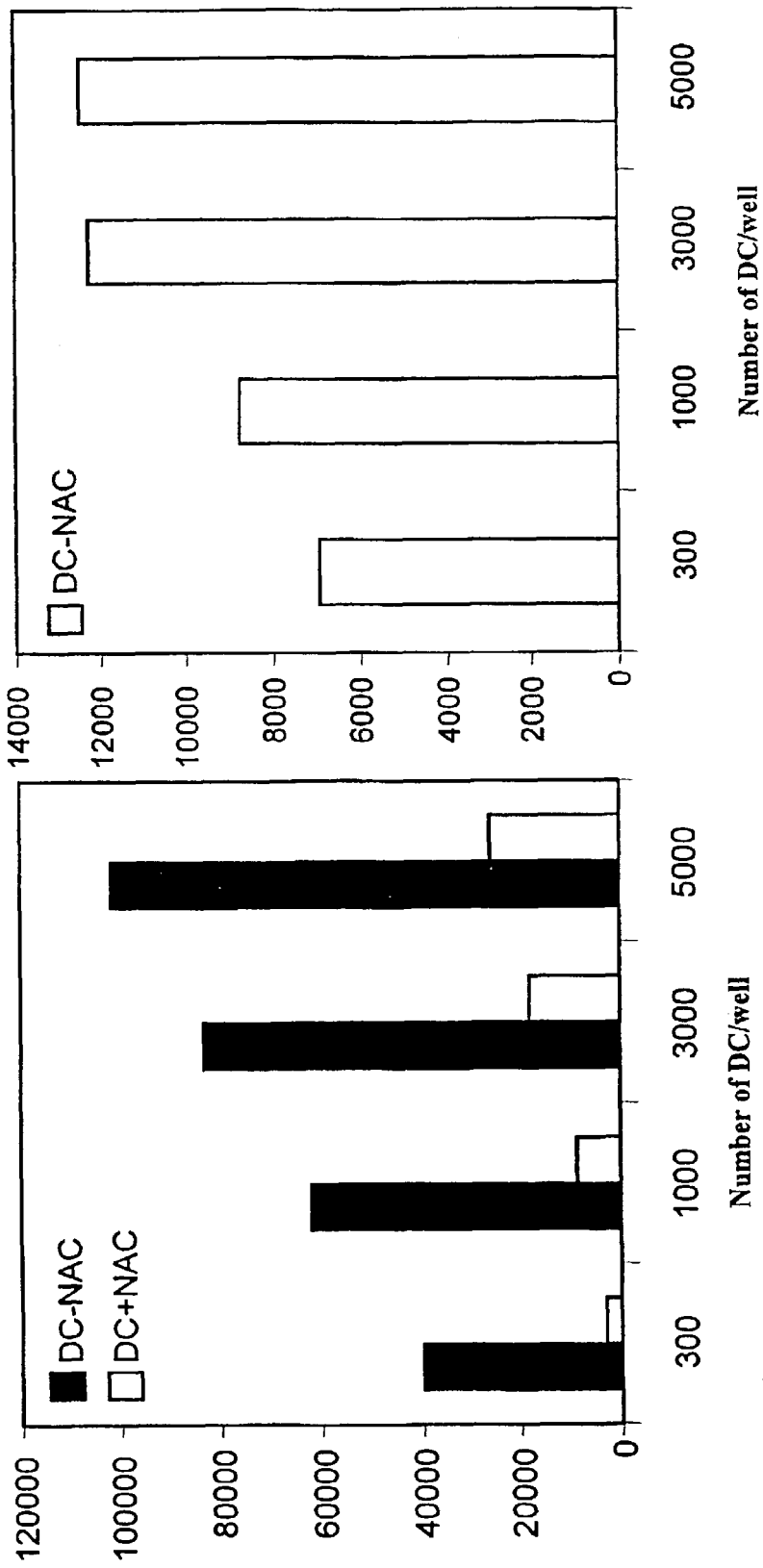
FIG. 22 depicts DC loaded with killed EBV cell lines and treated with the NFkB inhibitor induce tolerance of naïve CD4+ T cells. In the first stimulation cycle purified CD4+ CD45RA+ T cells (10$^6$/well) are cocultured in 24-well plates with sorted autologous immature DC (1×10$^5$/well) loaded with killed allogeneic cell line (colo 829) in the presence or absence of an inhibitor of NFkB translocation NAC (25 mM, SIGMA). After 5 days, the T cells from both cocultures (−NAC and +NAC) are harvested, washed and rested for an additional 2 days. T cells from primary cultures are rechallenged in a second proliferation assay with the DC loaded with killed EBV cells that are either autologous (Colo-EBV) or allogeneic (Hom2-EBV) to the Colo829 cell line used in the first stimulation. Proliferation is determined by uptake of (1 µCi/well for the last 16 hr) thymidine (vertical axis). The T cells are tolerized to antigens from Colo or Colo-EBV cells (Left panel) but can proliferate in responses to another antigen (right panel).

Induction of Antigen-Specific Tolerance with Antigen-Presenting Cells Loaded with Killed Allogeneic Cells Dendritic cells can also be loaded with cells that express an antigen to which the T cells could be tolerized. This is demonstrated in FIGS. 21 and 22 where loaded DCs are treated with compounds that allow antigen presentation but inhibit the expression of co-stimulatory molecules. In this way, the T cells can recognize the antigen but will become tolerant, as demonstrated in FIG. 22 the T cells are unable to proliferate when restimulated with the same antigen.

Purified CD45RA+CD4+ T cells are obtained from Ficoll-separated PBMC of healthy volunteers, depleted of other cells using CD8 (B9.11), CD45RO (UCHL1), CD14 (RMO52), CD16 (3G8), CD19 (J4.119), CD56 (NKH-1), anti-HLA-DR (B8.12.2), anti-glycophorin A (D2.10) monoclonal antibodies (mAbs) (Beckman-Coulter, Miami, Fla.) and Goat anti-mouse IgG Dynabeads (Dynal, Lake Success, N.Y.). The purity of the enriched populations was >90%.

Immature monocyte-derived DC are generated from adherent fraction of peripheral blood PBMC as described in the Example 1. Allogeneic cell lines (Colo 829, Colo-EBV and Hom2 EBV) are prepared as described in the Example 1. Antigen-loaded DCs are prepared as described above and used to stimulate naïve CD4 T cells as described above.

In the tolerance assay purified CD4+ CD45RA+ T cells ($10^6$/well) are cocultured in 24-well plates with sorted autologous immature DC ($1\times10^5$/well) loaded with killed allogeneic cell line (colo 829) in the presence or absence of an inhibitor of NFkB translocation NAC (25 mM, SIGMA). After 5 days, the T cells from both cocultures (−NAC and +NAC) are harvested, washed and rested for an additional 2 days. T cells from primary cultures are rechallenged in a second proliferation assay with the stimulators indicated in the FIG. 22 (colo EBV, Hom2 EBV). Proliferation is determined by uptake of (1 μCi/well for the last 16 hr) tritiated thymidine.

Example 6

Treatment of Patient with Antigen-Presenting Cells Loaded with Allogeneic Tumor Cells Antitumor responses in a patient can be obtained by administering antigen-presenting cells, including but not limited to DC, loaded with killed allogeneic tumor cells. The multiple and/or shared tumor antigens presented on the loaded antigen-presenting cells can elicit immune responses in the patient, leading to tumor rejection.

Example 7

Treatment of Patient with Antigen-Specific T Cells Expanded Ex Vivo by Antigen-Presenting Cells Loaded with Allogeneic Killed Tumor Cells Antitumor responses in a patient can be obtained by administering tumor antigen-specific T cells elicited ex vivo by DC loaded with killed allogeneic tumor cells. The shared tumor antigens presented on the tumor cells can be recognized by T cells specific for multiple and/or shared tumor antigens, leading to tumor rejection.

Example 8

Elimination of Transplantation Complications Using Antigen-Presenting Cells Loaded with Donor Cells Yet another aspect of the present invention can be useful in bone marrow and organ transplantation. In particular, the present invention permits the elimination of undesired T cells that react either against the transplant or against the host, which eliminates or minimizes the risk of graft rejection or of graft versus host disease.

Antigen-presenting cells of the donor or of the host are loaded with dead or dying EBV-transformed B cells from the host or from the donor, respectively. Immunosuppressive drugs such as azathioprine, cyclosporine or methotrexate are administered to the patient, permitting the killing of the activated T cells. Upon subsequent transplantation, there will be no graft rejection or graft versus host disease, respectively, because the reactive T cells have been eliminated.

Example 9

Elimination of Post-Transplantation Residual Disease in Hematological Malignancies Yet another aspect of the present invention can be useful in the elimination of the residual disease in post-transplant patients with hematological malignancies, including but not limited to leukemias and lymphomas.

The donor antigen-presenting cells are loaded with dead or dying leukemic cells of the donor or allogeneic cell lines.

Such loaded antigen-presenting cells are then administered to patients and the shared antigens presented on the loaded antigen-presenting cells elicits immune responses leading to the rejection of the tumor and elimination of the residual disease.

We claim:

1. A method of inducing a cytotoxic immune response against a tumor cell in a tumor bearing patient comprising:
   preparing immature monocyte-derived dendritic cells from a tumor-bearing patient;
   co-incubating said immature dendritic cells with one or more apoptotic allogeneic tumor cell lines to obtain antigen-loaded dendritic cells;
   co-culturing the antigen-loaded dendritic cells with total peripheral blood mononuclear cells isolated from said tumor bearing patient, wherein T cells are neither isolated nor enriched from the peripheral blood mononuclear cells prior to the co-culturing; wherein the co-culturing results in cytotoxic T cells against the allogeneic tumor cell line(s); and
   administering said cytotoxic T cells to the tumor-bearing patient.

2. The method of claim 1, wherein said cytotoxic immune response is directed against multiple tumor antigens.

3. A method of inducing a cytotoxic immune response against a tumor cell in a tumor bearing patient comprising:
   preparing immature monocyte-derived dendritic cells from a tumor-bearing patient;
   co-incubating said immature dendritic cells with one or more apoptotic allogeneic tumor cell lines to obtain antigen-loaded dendritic cells;
   providing a maturation stimulus to the antigen-loaded dendritic cells;
   co-culturing the matured antigen-loaded dendritic cells with total peripheral blood mononuclear cells isolated from said tumor bearing patient, wherein T cells are neither isolated nor enriched from the peripheral blood mononuclear cells prior to the co-culturing; wherein the co-culturing results in cytotoxic T cells against the allogeneic tumor cell line(s); and
   administering said cytotoxic T cells to the tumor-bearing patient.

4. The method of claim 3, wherein said tumor specific immune response is directed against multiple tumor antigens.

5. A method of inducing cytotoxic T cells comprising:
   obtaining peripheral blood mononuclear cells from an individual;
   culturing adherent cells from the peripheral blood mononuclear cells in the presence of GM-CSF and 11-4 to obtain immature monocyte-derived dendritic cells;
   co-incubating said immature dendritic cells with one or more apoptotic tumor cell lines to obtain antigen-loaded dendritic cells; and
   co-culturing the antigen-loaded dendritic cells with peripheral blood mononuclear cells obtained from the same individual, wherein T cells are neither isolated nor enriched from the peripheral blood mononuclear cells prior to the co-culturing; wherein the co-culturing results in cytotoxic T cells against the tumor cell line(s).

6. A method of obtaining isolated breast cancer antigen-loaded dendritic cells comprising
   obtaining immature monocyte-derived dendritic cells; and
   co-culturing the immature dendritic cells with an apoptotic breast cancer cell line or a mixture of apoptotic breast cancer cell lines to obtain antigen-loaded dendritic cells, wherein the ratio of immature dendritic cells and apoptotic cells in the co-culture is 1:1.

7. A method for obtaining T cell lines having cytotoxic activity against breast cancer comprising:
   obtaining peripheral blood lymphocytes and immature monocyte-derived dendritic cells from a patient with breast cancer;
   co-incubating the immature dendritic cells with cells from an apoptotic breast cancer cell line or a mixture of apoptotic breast cancer cell lines to obtain antigen-loaded dendritic cells, wherein the ratio of immature dendritic cells and apoptotic cells in the co-culture is 1:1; and
   co-culturing the antigen-loaded dendritic cells with the peripheral blood lymphocytes to obtain cytotoxic T cells against the breast cancer cell line(s) wherein T cells are not purified from the peripheral blood lymphocytes prior to the co-culture.

8. A method of inducing a cytotoxic T cell mediated tumor specific immune response in a patient comprising:
   obtaining peripheral blood lymphocytes and immature monocyte-derived dendritic cells from a patient with breast cancer;
   co-incubating the immature dendritic cells with cells from an apoptotic breast cancer cell line or a mixture of apoptotic breast cancer cell lines to obtain antigen-loaded dendritic cells, wherein the ratio of immature dendritic cells and apoptotic cells in the co-culture is 1:1;
   co-culturing the antigen-loaded dendritic cells with the peripheral blood lymphocytes to obtain cytotoxic T cells against the breast cancer cell line(s) wherein T cells are not purified from the peripheral blood lymphocytes prior to the co-culture; and
   administering the cytotoxic T lymphocytes to said patient.

9. A method for obtaining T cell lines having cytotoxic activity against breast cancer comprising:
   obtaining peripheral blood lymphocytes, and immature monocyte-derived dendritic cells from a patient with breast cancer;
   co-incubating the immature dendritic cells with cells from an apoptotic breast cancer cell line or a mixture of apoptotic breast cancer cell lines to obtain antigen-loaded dendritic cells, wherein the ratio of immature dendritic cells and apoptotic cells in the co-culture is 1:1; and
   co-culturing the antigen-loaded dendritic cells with the peripheral blood lymphocytes to obtain cytotoxic T cells against the breast cancer cell line(s) wherein T cells are not purified from the peripheral blood lymphocytes prior to the co-culture and wherein cytokines to help T cell proliferation are not added to the culture.

10. A method of inducing a cytotoxic T cell mediated tumor specific immune response in a patient comprising
    obtaining peripheral blood lymphocytes, and immature monocyte-derived dendritic cells from a patient with breast cancer;
    co-incubating the immature dendritic cells with cells from an apoptotic breast cancer cell line or a mixture of apoptotic breast cancer cell lines to obtain antigen-loaded dendritic cells, wherein the ratio of immature dendritic cells and apoptotic cells in the co-culture is 1:1;
    co-culturing the antigen-loaded dendritic cells with the peripheral blood lymphocytes to obtain cytotoxic T cells against the breast cancer cell line(s) wherein T cells are not purified from the peripheral blood lymphocytes prior to the co-culture and wherein cytokines to help T cell proliferation are not added to the culture; and
    administering the cytotoxic T cells to said patient.

11. The method of claim 6, wherein the breast cancer cell line(s) is/are incubated with IFNγ prior to undergoing apoptosis.

12. The method of claim 7, wherein the breast cancer cell line(s) is/are incubated with IFNγ prior to undergoing apoptosis.

13. The method of claim 8, wherein the breast cancer cell line(s) is/are incubated with IFNγ prior to undergoing apoptosis.

14. The method of claim 9, wherein the breast cancer cell line(s) is/are incubated with IFNγ prior to undergoing apoptosis.

15. The method of claim 10, wherein the breast cancer cell line(s) is/are incubated with IFNγ prior to undergoing apoptosis.

* * * * *